United States Patent [19]

Burkhard et al.

[11] 4,140,684
[45] Feb. 20, 1979

[54] AZO DYES HAVING A 6-HYDROXY-PYRIDONE-2 COUPLING COMPONENT RADICAL HAVING A SUBSTITUENT IN THE 1-POSITION

[75] Inventors: Hermann Burkhard, Neuallschwil; Roland Entschel, Allschwil; Willy Steinemann, Sigriswil, all of Switzerland

[73] Assignee: Fidelity Union Trust Company, Executive Trustee under the Sandoz Trust, Newark, N.J.

[21] Appl. No.: 564,716

[22] Filed: Apr. 3, 1975

Related U.S. Application Data

[63] Continuation-in-part of Ser. No. 787,586, Dec. 27, 1968, abandoned.

[30] Foreign Application Priority Data

Jul. 25, 1968 [CH] Switzerland .................. 11195/68
Nov. 13, 1968 [CH] Switzerland .................. 16898/68

[51] Int. Cl.² .............. C09B 29/36; D06P 1/18; D06P 3/42; D06P 3/54
[52] U.S. Cl. .................. 260/156; 546/296; 546/288; 546/287; 546/256; 546/261; 546/257; 546/258; 546/271; 546/284; 546/283; 546/193; 546/194; 546/280; 544/364; 544/360; 544/365; 544/131
[58] Field of Search .............. 260/156

[56] References Cited

U.S. PATENT DOCUMENTS 2,431,190 11/1947 Morgan ................. 260/156 X
3,487,066 12/1969 Ritter et al. ............. 260/156
3,905,901 9/1975 Berrie et al. ............ 260/156

Primary Examiner—Floyd D. Higel
Attorney, Agent, or Firm—Gerald D. Sharkin; Richard E. Vila; Melvyn M. Kassenoff

[57] ABSTRACT

Dyes of the formula

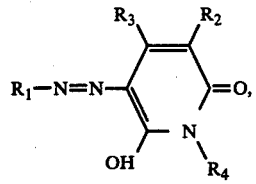

wherein
$R_1$ is a carbocyclic or heterocyclic diazo component radical,
$R_2$ is cyano or acyl,
$R_3$ is alkyl, carbocyclic aryl or heterocyclyl, or a substituted derivative thereof, and
$R_4$ is hydrocarbyl or substituted hydrocarbyl, with the proviso that $R_4$ is free of sulfo groups and protonizable groups, are useful as disperse dyes for the dyeing and printing of fibres and textiles of synthetic and semi-synthetic, hydrophobic organic substances of high molecular weight. These dyes build up excellently and yield dyeings which are fast to thermofixation, sublimation, pleating, ozone, rubbing, gas fumes, water, sea water, perspiration, alkali and washing.

16 Claims, No Drawings

AZO DYES HAVING A 6-HYDROXY-PYRIDONE-2 COUPLING COMPONENT RADICAL HAVING A SUBSTITUENT IN THE 1-POSITION

This application is a continuation-in-part of copending application Ser. No. 787,586, filed Dec. 27, 1968 and now abandoned.

The new compounds have the formula

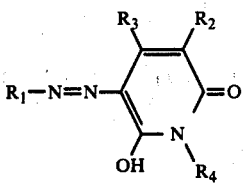

In this formula
$R_1$ is the radical of a diazo component,
$R_2$ is a cyano or acyl group,
$R_3$ is an alkyl, aryl or heterocyclic radical which may be substituted,
$R_4$ is a hydrocarbon radical which may be substituted or an amino group; sulphonic acid groups and radicals which add on a proton are excluded as possible substituents.

In the specially preferred compounds of formula (I)
$R_1$ is the radical of a diazo component,
$R_2$ is a cyano or acyl group,
$R_3$ is an alkyl group having 1 to 6 carbon atoms which may be substituted by chlorine or bromine atoms, cyano or alkoxy groups; a phenyl or benzyl radical which may be substituted by chlorine or bromine atoms, hydroxyl, alkyl, alkoxy, alkylamino, dialkylamino, nitro, cyano, acyl, acyloxy or acylamino groups, a naphthyl, alkoxynaphthyl, thienyl, methylthienyl, benzothiazolyl, methoxybenzothiazolyl, acylbenzothiazolyl, acyloxybenzothiazolyl, furyl, thiazolyl, pyridyl, imidazolyl or benzimidazolyl radical,
$R_4$ is an alkyl or an alkenyl group group having 1 to 10 carbon atoms having 2 to 10 carbon atoms, which may be substituted but is free from protonizable groups, a phenyl radical which may be substituted but is free from protonizable groups, or a radical of the formula

where
$R_5$ represents a hydrogen atom or has one of the meanings of $R_6$
and
$R_6$ represents a hydrocarbon radical which has 1 to 8 carbon atoms and may be substituted, preferably an alkyl or phenyl radical; a formyl, alkylcarbonyl or benzoyl radical,
or where $R_5$ and $R_6$ jointly with the thereto attached nitrogen atom represent a heterocyclic ring system containing up to 5 carbon atoms.

The compounds of formula (I) are free from sulphonic acid groups.

Examples of suitable diazo component radicals $R_1$ are phenyl, naphthyl, thiazolyl, benzothiazolyl, thiadiazolyl, pyrazolyl, imidazolyl and thiophenyl radicals. The aliphatic and alkylene radicals are unsaturated or preferably saturated radicals having 1 to 8 or more particularly 1, 2, 3 or 4 carbon atoms.

Preferred acyl radicals are those of formulae

or

where
R represents a hydrocarbon radical which may contain substituents and/or hetero atoms, preferably an alkyl or phenyl radical,
X is a group of the formula —CO—, —O—CO— or —SO$_2$—,
R' is a hydrogen atom or R,
Y is a group of the formula —NR"—CO— or —NR"—SO$_2$—, and R" is a hydrogen atom or R.

The radicals of aromatic character may all bear substituents, e.g. halogen atoms, in particular fluorine, chlorine or bromine atoms, nitro, cyano, thiocyano, hydroxyl, alkyl, alkoxy, phenyl, phenoxy alkylamino, dialkylamino, phenylamino, acyl, acyloxy or acylamino groups.

The aforementioned alkyl, alkenyl and alkoxy groups generally contain 1 to 8 or more particularly 1, 2, 3 or 4 carbon atoms; like the aforementioned aliphatic radicals they may bear as substituents, e.g., halogen atoms, preferably chlorine or bromine atoms, cyano, thiocyano, hydroxyl, alkoxy, phenyl, phenoxy, acyl or acyloxy groups. The alkyl radicals are understood to comprise cycloalkyl radicals, in particular cyclohexyl radicals.

By protonizable groups are understood nitrogenous radicals which add on a proton in acid medium, particularly in mineral acid medium. The dyes of the present invention are virtually insoluble in water.

Preferred dyes have the formula

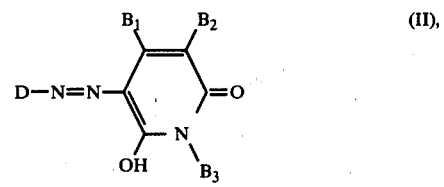

where
D is a phenyl radical which may be substituted by chlorine or bromine atoms, hydroxyl, cyano, thiocyano, nitro, methyl, ethyl, trifluoromethyl, methoxy, ethoxy, formyl, acetyl, propionyl, benzoyl, methylbenzoyl, methoxycarbonyl, ethoxycarbonyl, ethoxycarbonyloxy, benzyloxycarbonyloxy, acetoxy, propionyloxy, benzoyloxy, methoxyethoxycarbonyl, acetylamino, propionylamino, benzoylamino, methoxycarbonylamino, ethoxycarbonylamino, methylsulphonyl, ethylsulphonyl, propylsulphonyl, butylsulphonyl, chloromethylsulphonyl, aminosulphonyl, methylaminosulphonyl, dimethylaminosulphonyl, di-(hydroxyethyl)-aminosulphonyl, cyclohexylaminosulphonyl, phenylaminosulphonyl, chloromethylaminosulphonyl, methoxyphenylaminosulphonyl, benzylaminosulphonyl, N-piperidylsulphonyl, N-morpholinosulphonyl, methylsulphonyloxy, ethylsulphonyloxy, ethoxyethylsulphonyloxy, propylsulphonyloxy, hexylsulphonyloxy, cyclohexylsulphonyloxy, chloromethylsulphonyloxy, cyanoethylsulphonyloxy, phenylsulphonyloxy, aminosulphonyloxy, N-morpholinosulphonyloxy, methoxyphenylsulphonyloxy, ethyleneaminosulphonyloxy, methylaminosulphonyloxy, ethylaminosulphonyloxy, propylaminosulphonyloxy, butylaminosulphonyloxy, dimethylaminosulphonyloxy, diethylaminosulphonyloxy, dipropylaminosulphonyloxy, dibutylaminosulphonyloxy, phenylaminosulphonyloxy, N-phenyl-N-methylaminosulphonyloxy, N-phenyl-N-ethylaminosulphonyloxy, methoxyphenylaminosulphonyloxy, phenylamino, nitrophenylamino, dinitrophenylamino, phenyl, acetylaminophenyl, phenylaminosulphonylphenyl, phenylazo or nitrophenylazo groups, a naphthyl radical which may be substituted by methoxy, ethoxy, phenylazo or dimethylaminosulphonyl groups, a thiazolyl radical which may be substituted by chlorine or bromine atoms, nitro, cyano, methyl, phenyl, methylsulphonyl or ethylsulphonyl groups, a benzothiazolyl radical which may be substituted by chlorine or bromine atoms, cyano, nitro, methyl, ethyl, methoxy, ethoxy, methylsulphonyl, ethylsulphonyl, cyanoethylsulphonyl, aminosulphonyl or methylaminosulphonyl groups, a pyrazolyl radical which may be substituted by cyano, methyl or phenyl groups, a thiadiazolyl radical which may be substituted by a methyl group, an imidazolyl radical which may be substituted by nitro or methyl groups, a thienyl radical which may be substituted by nitro or acetyl groups, or the radical of the formula

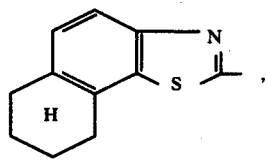

$B_1$ is an alkyl radical having 1 to 4 carbon atoms which may be substituted by chlorine or bromine atoms, hydroxyl, cyano, methoxy or ethoxy groups, a phenyl radical which may be substituted by chlorine or bromine atoms, methyl, methoxy, nitro, methoxycarbonyl, ethoxycarbonyl, methylaminosulphonyl, dimethylaminosulphonyl, cyano or acetylamino groups, or a naphthyl, methoxynaphthyl, ethoxynaphthyl, thienyl, methylthienyl, furyl, thiazolyl, pyridyl, imidazolyl or benzimidazolyl radical, $B_2$ is cyano, acetyl, propionyl, methylsulphonyl, ethysulphonyl, benzoyl, phenylsulphonyl, nicotinoyl, aminocarbonyl, methylaminocarbonyl, dimethylaminocarbonyl, ethylaminocarbonyl or diethylaminocarbonyl, and $B_3$ is an alkyl radical having 1, 2, 3 or 4 carbon atoms which may be substituted by chlorine or bromine atoms, hydroxyl, cyano, methoxy, ethoxy, methoxyethoxy, cyanoethoxy, phenoxyethoxy, acetyl, propionyl, benzoyl, formyloxy, acetoxy, propionyloxy, methoxypropionyloxy, acryloxy, benzoyloxy, methoxycarbonyl, ethoxycarbonyl, ethoxyethoxycarbonyl, cyanomethoxycarbonyl, phenoxycarbonyl, methoxycarbonyloxy, ethoxycarbonyloxy, phenoxycarbonyloxy, aminocarbonyl, methylaminocarbonyl, dimethylaminocarbonyl, methylaminocarbonyloxy, ethylaminocarbonyloxy, phenylaminocarbonyloxy, methoxycarbonylethoxy, 5-chlorofuryl-(2)-, methylsulphonyloxy, ethylsulphonyloxy, phenylsulphonyloxy, vinylsulphonyloxy, phenoxysulphonyl, phenthioethylsulfonyl or vinylsulphonyl groups, a cyclohexyl, trimethylcyclohexyl, methylamino, dimethylamino, ethylamino, diethylamino, hydroxyethylamino, di-($\beta$-cyanoethyl)-amino, di-(acetoxyethyl)-amino, phenylamino, ethoxyethylamino, formylamino, acetylamino, propionylamino, benzoylamino, N-piperazyl, N-piperidyl or N-morpholinyl radical or the radical of the formula

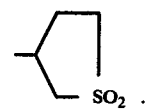

Representative of the compounds of Formula II are the compounds of the formula

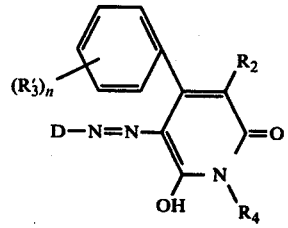

(IIa), wherein
D is substituted phenyl, wherein each substituent of substituted phenyl is chloro, bromo, nitro, lower alkyl, lower alkoxy, cyano, lower alkoxycarbonyl, sulfamoyl, N-lower alkylsulfamoyl, N,N-dilower alkylsulfamoyl, N-lower alkylsulfamoyloxy or N,N-dilower alkylsulfamoyloxy,
$R_2$ is cyano or lower alkanoyl,
$R_3'$ is chloro, lower alkyl or lower alkoxy,
$R_4$ is lower alkyl or monosubstituted lower alkyl, wherein the substituent of monosubstituted lower alkyl is hydroxy or lower alkoxy, and
n is 0 or 1.

Further representative compounds of Formula II are those
wherein
$B_3$ is methylamino, dimethylamino, ethylamino, diethylamino, hydroxyethylamino, di-($\beta$-cyanoethyl)-amino, di-(acetoxyethyl)amino, phenylamino, ethoxyethylamino, formamido, acetamido, propionamido, benzamido, N-piperazino, N-piperidino or N-morpholino, and
D, $B_1$ and $B_2$ are as defined in connection with Formula II.

Additional representative compounds of Formula II are those
wherein
$B_2$ is methylsulfonyl, ethylsulfonyl or phenylsulfonyl, and
D, $B_1$ and $B_3$ are as defined in connection with Formula II.

Still further representative compounds of Formula II are those wherein

B₁ is (a) phenyl, (b) substituted phenyl each substituent of which is independently chloro, bromo, methyl, methoxy, nitro, methoxycarbonyl, ethoxycarbonyl, methylsulfamoyl, dimethylsulfamoyl, cyano or acetamido, (c) naphthyl, (d) methoxynaphthyl, (e) ethoxynaphthyl, (f) thienyl, (g) methylthienyl, (h) furyl, (i) thiazolyl, (j) pyridyl, (k) imidazolyl or (l) benzimidazolyl, and D, B₂ and B₃ are as defined in connection with Formula II.

The compounds of formula (I) are produced by diazotizing an amine of the formula

$$R_1-NH_2 \quad (III)$$

and coupling the diazonium compound with a compound of formula

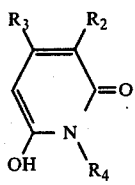

(IV).

The compounds of the formula (II) are produced analogously by coupling a diazotized amine of formula

$$D-NH_2 \quad (V)$$

with a compound of the formula

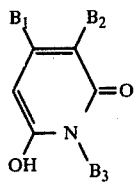

(VI).

The coupling reaction generally takes place in acid, if necessary buffered medium, with cooling. Sodium acetate is a suitable buffering agent.

It is assumed that the compounds of the formulae (I) and (II) are present in a tautomeric state, which can be expressed by the following formulae

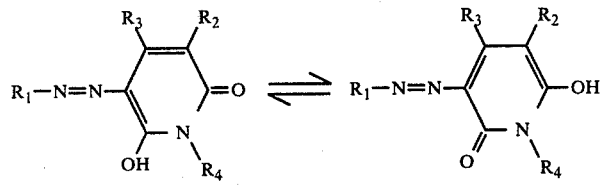

The coupling components of formulae (IV) and (VI) are produced in analogy with the method of J. Guareschi, Atti Acc. R. d. Scienze di Torino, 1895/96; c.f. Chem. Ber. 29,655(1896), Chem. Zentr. 1896, 1,602 and 1896, II, 46, and Umaprasynna Basu, J. Indian Chem. Soc. 8 312-328 (1931), by condensation of appropriately substituted acetic acid amides or acetic acid hydrazides with suitably substituted β-ketocarboxylic acid esters.

It is advantageous to convert the new dyes into dye preparations before application using known methods, e.g. grinding in the presence of a dispersing agent and/or fillers, followed by drying in a vacuum or atomizer drier. The resulting dye preparations, after the addition of a suitable amount of water, can be employed for dyeing, padding or printing from long or short baths. From aqueous dispersion the dyes build up excellently on fibres of synthetic and semi-synthetic hydrophobic substances of high molecular weight. The dyes are highly suitable for the exhaustion dyeing, pad dyeing and printing of textiles of linear aromatic polyesters, cellulose diacetate, cellulose triacetate and synthetic polyamides. They are also dyeable on polyolefins and polyvinyl compounds.

The known dyeing and printing methods are used, e.g. the process described in French Patent 1,445,371. The dyeings obtained are of yellow to red shade and have very good fastness properties, being outstandingly fast to thermofixation, sublimation, pleating, ozone, rubbing and gas fumes. The wet fastness properties including fastness to water, sea water, perspiration, alkali and washing are also very good. Other notable features are fastness to cross dyeing, dry cleaning and light, reduction stability and good migration. The dyes are stable to the action of the various forms of permanent press finishing. Their good covering power on barry polyester materials is a further advantage. They are suitable for application to texturized polyester fibres.

In the following Examples the parts and percentages are by weight and the temperatures in degrees centigrade.

EXAMPLE 1

17.3 Parts of 2-chloro-4-nitroaniline are mixed with 100 parts of water and 25 parts of 30% hydrochloric acid. After cooling to 0° a solution of 8 parts of sodium nitrite in 20 parts of water is dropped in over 15 minutes, after which stirring is continued for 30 minutes. The excess nitrous acid is then decomposed with aminosulphonic acid. After filtration to eliminate a small amount of a solid impurity, the clarified diazonium salt is cooled to 0°-5° and a solution of 17.8 parts of 1,4-diethyl-3-cyano-6-hydroxypyridone-2 in 200 parts of dimethylformamide is added in small portions. During the addition and until the completion of the reaction, the mixture is maintained at 0°-5°. Subsequently the precipitated dye is filtered off, washed until neutral and dried. It is obtained in the form of orange crystals which give dyeings of yellow shade on synthetic fibres having excellent fastness properties.

EXAMPLE 2

A solution of 8.4 parts of 2-aminotriazole-1,3,4 in 100 parts of water and 25 parts of 30% hydrochloric acid is prepared and raised to 70°. On cooling to about 5° a solution of 8 parts of sodium nitrite in 20 parts of water is added dropwise over a period of 15 minutes, then stirring is continued for a further 30 minutes. The excess nitrous acid is decomposed with aminosulphonic acid. A small amount of a solid impurity is filtered off to give a clear diazonium salt solution which is cooled to 0°–5°. A solution of 16.4 parts of 1,4-dimethyl-3-cyano-6-hydroxypyridone-2 in 100 parts of glacial acetic acid is added. The dye settles out immediately in crystalline form; it is filtered off, washed until neutral and dried. The orange crystals dye snythetic fibres in fast yellow shades.

EXAMPLE 3

17.3 Parts of 2-chloro-4-nitroaniline are mixed with 100 parts of water and 25 parts of 30% hydrochloric acid. The mixture is cooled to 0°, whereupon a solution of 8 parts of sodium nitrite in 20 parts of water is added dropwise in 15 minutes. Stirring is continued for 30 minutes, after which the excess nitrous acid is destroyed with amidosulphonic acid. The solution is filtered to eliminate a small amount of a solid impurity and then cooled to 0°–5°. A solution of 16.4 parts of 1,4-dimethyl-3-cyano-6-hydroxypridone-2 in 100 parts of water, adjusted to pH 4.0–4.5 with acetic acid, is added. This pH is maintained constant throughout the coupling reaction by the addition of sodium acetate. When the reaction has run its course the dye is filtered off, washed until neutral and dried. The yellow crystals dye synthetic fibres in yellow shades with excellent fastness properties.

A dye with similar fastness properties is obtained when in place of 2-chloro-4-nitroaniline an equimolar amount of diazotized sulphanilic acid dimethylamide is employed.

EXAMPLE 4

17.1 Parts of 1-aminobenzene-4-methylsulphone are dissolved in 150 parts of water and 25 parts of 30% hydrochloric acid. The solution is cooled to 0° and over 1 hour a solution of 8 parts of sodium nitrite in 20 parts of water is added. Stirring is continued for a further hour, then the excess nitrous acid is decomposed with aminosulphonic acid. Over 30 minutes the clear diazonium salt solution is gradually added to an ice-cold solution of 19.3 parts of 1-dimethylamino-3-cyano-4-methyl-6-hydroxypyridone-2 in 150 parts of water, adjusted to pH 4 with acetic acid and buffered with sodium acetate. The dye settles out as a yellow powder. After the addition of the diazonium solution stirring is continued for 30 minutes and the product isolated. The yellow dye dyes synthetic fibres in bright yellow shades having good fastness properties.

A dye with similar fastness properties is obtained when in place of 1-aminobenzene-4-methylsulphone the equimolecular amount of 2-chloro-4-nitroaniline is employed.

EXAMPLE 5

13.8 Parts of 2-nitroaniline are dissolved in 100 parts of water and 25 parts of 30% hydrochloric acid by stirring and the solution is cooled to 0°–5°. The amine is diazotized with a solution of 8 parts of sodium nitrite in 30 parts of water. Stirring is continued for 1 hour, then the excess nitrous acid is destroyed with amidosulphonic acid. The diazonium salt solution is filtered free from any solid impurities present and added in small portions to a solution of 19.3 parts of 1-ethylamino-3-cyano-4-methyl-6-hydroxypyridone-2 in 150 parts of water, adjusted to pH 4.5 with glacial acetic acid, the temperature of which is 0°–5°. The dye settles out as a yellow powder during the addition of the diazonium salt solution. During the reaction the pH is maintained at pH 4.5 by adding sodium acetate. After the addition of the diazonium solution stirring is continued for 45 minutes, then the dye is isolated. On synthetic fibres it gives dyeings of bright greenish yellow shade which have excellent fastness properties.

EXAMPLE 6

21.6 Parts of 3-dimethylaminosulphonyloxyaniline are dissolved in 280 parts of water and 36 parts of 30% hydrochloric acid. The solution is cooled to 0°–5° and a solution of 80 parts of sodium nitrite in 60 parts of water is added for diazotization. For completion of this reaction stirring is continued at 0°–5° for 1 hour, after which the excess nitrous acid is decomposed with amidosulphonic acid. For the coupling reaction 25.5 parts of 1-dimethylamino-3-cyano-4-phenyl-6-hydroxypyridone-2 are suspended in 250 parts of water and adjusted to pH 4.5 with acetic acid. The diazonium salt solution is added dropwise to the well cooled coupling suspension over 30 minutes, during which time the pH is kept constant with sodium acetate. Stirring is continued for 1 hour, following which the precipitated dye is filtered off. It is obtained as a yellow powder which gives dyeings of yellow shade on synthetic fibres having excellent fastness properties.

EXAMPLE 7

13.8 Parts of 3-nitroaniline are finely suspended by stirring in 100 parts of water and 35 parts of 30% hydrochloric acid. The suspension is cooled to 0°–5° and the amine diazotized with a solution of 8 parts of sodium nitrite in 30 parts of water. After the addition of the nitrite stirring is continued for 1 hour and the excess nitrous acid is then destroyed with amidosulphonic acid. For coupling, 29.8 parts of finely pulverized 1(γmethoxypropyl)-3-cyano-4-p-tolyl-6-hydroxypyridone-2 is suspended in 300 parts of water and the pH adjusted to 4.5 with glacial acetic acid. After the temperature of the suspension has been reduced to 0°–5°, the diazonium salt solution, clarified by filtration, is dropped in over 30 minutes. Stirring is continued for a further hour, during which time the pH is maintained at 4.0–5.0 with sodium acetate. Finally the yellow dye formed is isolated, washed and dried. Its dyeings on synthetic fibres are of bright yellow shade and have excellent fastness properties.

When in place of the 29.8 parts of 1-(γ-methoxypropyl)-3-cyano-4-p-tolyl-6-hydroxypyridone-2 used in this example, 22.2 parts of 1-(γ-methoxypropyl)-3-cyano-4-methyl-6-hydroxypyridone-2 are employed, a yellow dye with similar fastness properties is obtained.

Application Examples (A) A mixture of 7 parts of the dye of Example 3, 4 parts of sodium dinaphthylmethane disulphonate, 4 parts of sodium cetyl sulphate and 5 parts of anhydrous sodium sulphate is ground in a ball mill for 48 hours to give a fine powder. One part of the powder is suspended in a little water and the suspension run through a sieve into a bath of 1000 parts of water containing 3 parts of sodium lauryl sulphate. The liquor ratio is 1:40. At 40°–50° 100 parts of a scoured fabric of polyester fibre are entered into the bath, and after the addition of 20 parts of an emulsion of chlorinated benzene in water the bath is raised slowly to 100° and the fabric dyed for 1–2 hours at 95°–100°. It is then removed, rinsed, soaped, rinsed again and dried. The level yellow dyeing has excellent fastness to light, cross dyeing, washing, water, sea water, perspiration, sublimation, gas fumes, pleating and permanent press finishing.

(B) A mixture of 30 parts of the dye of Example 7, 40 parts of sodium dinaphthylmethane disulphonate, 50 parts of sodium cetyl sulphate and 50 parts of anhydrous sodium sulphate is ground in a ball mill to give a fine powder. 4 Parts of the powder are suspended in 1000 parts of water at 40°–50°. 100 Parts of a scoured fabric of polyester fibre are entered into the bath which is then raised slowly to 130°. The fabric is dyed for about 1 hour at this temperature under pressure. On removal it is rinsed, soaped, rinsed and dried. A yellow dyeing with the same fastness properties as that of Example A is obtained.

(C) A mixture of 20 parts of the dye of Example 1, 55 parts of sulphite cellulose waste lye and 800 parts of water is ground in a ball mill until the size of the dye particles is less than 1 micron. The colloidal solution thus obtained is mixed with 25 parts of ethylene glycol-monobutylether and 400 parts of carboxymethyl cellulose. This printing paste is highly suitable for the Vigoureux printing of polyester slubbing. The slubbing is printed with two rollers giving a coverage of 78% and without intermediate drying is steamed at 120°. Yellow prints having good fastness properties are obtained.

(D) A mixture of 7 parts of the dye of Example 3, 13 parts of sulphite cellulose waste lye and 100 parts of water is ground in a ball mill and the resulting paste is dried in an atomizer. 4 Parts of the dye preparation thus obtained are pasted with a little water and added through a sieve to a bath of 4000 parts of water containing 4 parts of N-oleyl-N'-hydroxyethyl-N'-(3'-sulpho-2'-hydroxypropyl)-ethylenediamine. At 20° 100 parts of a fabric of nylon 66 fibre are entered into the bath, which is then raised over 30 minutes to 100°. The fabric is dyed for 1 hour at this temperature and subsequently rinsed and dried. A level yellow dyeing is obtained which has good fastness to light, cross dyeing, washing, water, sea water, perspiration, sublimation, rubbing and solvents.

(E) A fine aqueous suspension of 30 parts of the dye of Example 4, 70 parts of sodium dinaphthylmethanedisulphonate and 3 parts of sodium alginate is made up to 1000 parts with water and well stirred. A polyester fabric is padded with this liquor at 20°, air dried at 60°–100° and treated for 1 minute in dry air at 230°. It is then rinsed, soaped, rinsed again and dried. A fast, level dyeing is obtained. Fabrics of synthetic polyamide fibres can be dyed by the same method.

In the following Table further dyes are listed which can be produced in accordance with the procedures of Examples 1 to 7. All these dyes have the fastness properties mentioned in the foregoing and give dyeings of yellow to red shade on polyester fibres.

The dyes listed in Table I are of the formula

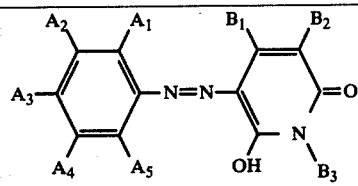

| Examp. No. | $A_1$ | $A_2$ | $A_3$ | $A_4$ |
|---|---|---|---|---|
| 8 | H | H | $-OCOOC_2H_5$ | H |
| 9 | H | H | $-OCOC_2H_5$ | H |
| 10 | H | H | $-COCH_3$ | H |
| 11 | $-Br$ | H | $-NO_2$ | H |
| 12 | H | H | $-NO_2$ | H |
| 13 | H | $-NO_2$ | H | H |
| 14 | $-NO_2$ | H | H | H |
| 15 | $-CN$ | H | $-NO_2$ | H |
| 16 | H | $-NO_2$ | H | H |
| 17 | H | $-NO_2$ | H | H |
| 18 | H | $-NO_2$ | H | H |
| 19 | H | $-NO_2$ | H | H |
| 20 | H | $-NO_2$ | H | H |
| 21 | H | H | $-NO_2$ | H |
| 22 | H | H | $-NO_2$ | H |
| 23 | $-NO_2$ | H | H | H |
| 24 | $-Cl$ | H | $-NO_2$ | H |
| 25 | H | H | $-COOCH_3$ | H |
| 26 | $-Cl$ | H | $-NO_2$ | H |
| 27 | $-NO_2$ | H | $-SO_2CH_3$ | H |
| 28 | $-CN$ | H | H | $-Cl$ |
| 29 | $-Cl$ | H | $-SO_2CH_3$ | H |
| 30 | H | H | $-NHCOC_6H_5$ | H |
| 31 | H | H | $-NHCOC_6H_5$ | H |
| 32 | H | H | $-NHCOCH_3$ | H |
| 33 | $-Cl$ | H | $-SO_2N(CH_3)_2$ | $-Cl$ |
| 34 | $-Cl$ | H | $-SO_2N(CH_3)_2$ | H |
| 35 | H | $-O-SO_2-N(CH_3)_2$ | H | H |
| 36 | H | $-O-SO_2-N(CH_3)_2$ | H | H |
| 37 | H | $-O-SO_2-N(CH_3)_2$ | H | H |
| 38 | H | $-O-SO_2-N(CH_3)_2$ | H | H |
| 39 | H | $-O-SO_2-N(CH_3)_2$ | H | H |
| 40 | H | $-O-SO_2-N(CH_3)_2$ | H | H |
| 41 | H | $-O-SO_2-N(CH_3)_2$ | H | H |
| 42 | H | $-O-SO_2-N(CH_3)_2$ | H | H |
| 43 | $-OCH_3$ | H | $-NO_2$ | H |
| 44 | H | H | $-COOCH_2C_6H_5$ | H |
| 45 | $-CH_3$ | H | $-OH$ | H |
| 46 | H | H | $-SO_2NHCH_3$ | H |
| 47 | H | H | $-OCH_3$ | H |
| 48 | H | H | $(H_3C)_2NCO-$ | H |

-continued

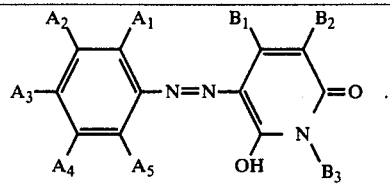

| No. | | | | |
|---|---|---|---|---|
| 49 | H | —OSO$_2$CH$_3$ | H | H |
| 50 | H | H | H$_2$NSO$_2$ | H |
| 51 | H | —NO$_2$ | H | H |
| 52 | H | —NO$_2$ | H | H |
| 53 | H | —NO$_2$ | H | H |
| 54 | H | —NO$_2$ | H | H |
| 55 | H | —NO$_2$ | H | H |
| 56 | H | H | H$_3$COCO— | H |
| 57 | H | H | H$_3$COCO— | H |
| 58 | H | H | H$_3$COCO— | H |
| 59 | H | H | H$_3$COCO— | H |
| 60 | —NO$_2$ | H | —CH$_3$ | H |
| 61 | —NO$_2$ | H | —CH$_3$ | H |
| 62 | —NO$_2$ | H | —CH$_3$ | H |
| 63 | —NO$_2$ | H | —CH$_3$ | H |
| 64 | —NO$_2$ | H | —CH$_3$ | H |
| 65 | —NO$_2$ | H | —CH$_3$ | H |
| 66 | —NO$_2$ | H | —CH$_3$ | H |
| 67 | H | —NO$_2$ | H | H |
| 68 | Cl | H | H | —Cl |
| 69 | Cl | H | H | —Cl |
| 70 | Cl | H | H | —Cl |
| 71 | Cl | H | H | —Cl |
| 72 | Cl | H | H | —Cl |
| 73 | Cl | H | H | —Cl |
| 74 | —COOCH$_3$ | H | —NO$_2$ | H |
| 75 | H | H | CH$_3$OCO— | H |
| 76 | —COOCH$_3$ | H | H | CH$_3$OCO— |
| 77 | H | H | —NO$_2$ | H |
| 78 | H | —NO$_2$ | H | H |
| 79 | —CN | H | —NO$_2$ | H |
| 80 | H | H | —Cl | H |
| 81 | H | —Br | H | H |
| 82 | H | H | —CN | H |
| 83 | H | H | —CH$_3$ | H |
| 84 | —CN | H | —NO$_2$ | H |
| 85 | H | H | —Cl | H |
| 86 | H | —Br | H | H |
| 87 | H | H | —CN | H |
| 88 | H | H | —CH$_3$ | H |
| 89 | —CN | H | —NO$_2$ | H |
| 90 | H | H | —Cl | H |
| 91 | H | H | H$_3$COCONH— | H |
| 92 | H | H | CH$_3$OC$_2$H$_4$OCO— | H |
| 93 | H | H | CH$_3$CONH—⟨C$_6$H$_4$⟩— | H |
| 94 | —NO$_2$ | H | —Cl | H |
| 95 | —NO$_2$ | H | —NO$_2$ | H |
| 96 | H | —NO$_2$ | H | H |
| 97 | H | H | H | H |
| 98 | H | H | H | H |
| 99 | H | H | H | H |
| 100 | H | H | —Cl | H |
| 101 | H | H | —Cl | H |
| 102 | H | H | —Cl | H |
| 103 | —Cl | H | H | —Cl |
| 104 | —Cl | H | H | —Cl |
| 105 | —Cl | H | H | —Cl |
| 106 | H | H | H$_5$C$_2$OOC— | H |
| 107 | H | H | H$_5$C$_2$OOC— | H |
| 108 | H | H | H$_5$C$_2$OOC— | H |
| 109 | H | H | (H$_3$C)$_2$NSO$_2$— | H |
| 110 | H | H | (H$_3$C)$_2$NSO$_2$— | H |
| 111 | H | —NO$_2$ | H | H |
| 112 | H | —NO$_2$ | H | H |
| 113 | H | H | —NO$_2$ | H |
| 114 | H | H | H$_5$C$_2$SO$_2$— | H |
| 115 | H | H | —Cl | H |
| 116 | H | H | —Cl | H |
| 117 | —OCH$_3$ | H | H | H |
| 118 | H | H | NCS— | H |
| 119 | H | H | ″ | H |
| 120 | —Cl | H | ″ | —Cl |
| 121 | H | H | —CHO | H |
| 122 | —NO$_2$ | H | —NO$_2$ | —OCH$_3$ |
| 123 | H$_3$CSO$_2$— | H | ″ | H |
| 124 | H | H | H$_3$C—SO$_2$— | H |
| 125 | —Cl | H | NCS— | H |
| 126 | —NO$_2$ | H | —NO$_2$ | —Cl |
| 127 | —Cl | H | H | —Cl |
| 128 | —OCH$_3$ | H | H | —Cl |
| 129 | H | —Cl | —Cl | H |
| 130 | —NO$_2$ | H | —NO$_2$ | —NHCOCH$_3$ |

-continued

Structure: A₂, A₁ on one benzene ring with A₃, A₄, A₅; connected via —N=N— to a pyridone ring with B₁, B₂ substituents, C=O, N—B₃, and OH.

| No. | A₁ | A₂,A₃,A₄,A₅ etc. | B₁ | B₂ | B₃ |
|---|---|---|---|---|---|
| 131 | —COCH₃ | H | " | H | |
| 132 | —Cl | H | —C₆H₅ | H | |
| 133 | H | H | —NO₂ | H | |
| 134 | H | —NO₂ | H | H | |
| 135 | H | H | (CH₂)₂N—SO₂O— (aziridinyl sulfonate) | H | |
| 136 | H | H₅C₆N(CH₃)SO₂O— | H | H | |
| 137 | H | H₅C₆NH—SO₂O— | H | H | |
| 138 | H | H | (HOC₂H₄)₂NSO₂— | H | |
| 139 | H | H | piperidino-SO₂— | H | |
| 140 | H | —Cl | —Cl | —Cl | |
| 141 | H | —Cl | —Cl | H | |
| 142 | —CH₃ | H | —CH₃ | H | |
| 143 | —OCH₃ | H | CH₃O—C₆H₄—SO₂O— | H | |
| 144 | H | —CH₃ | Cl—C₆H₄—SO₂O— | —CH₃ | |
| 145 | H | " | —OSO₂C₆H₅— | H | |
| 146 | H | C₆H₅CH₂SO₂O— | —CH₃ | | |
| 147 | —CN | H | H | —Cl | |
| 148 | —Cl | H | CH₃SO₂— | H | |
| 149 | —Cl | H | (CH₃)₂NSO₂— | —Cl | |
| 150 | —Cl | H | " | —Cl | |
| 151 | H | H | C₆H₅—CONH— | H | |
| 152 | H | H | H₃CCONH— | H | |
| 153 | H | H | H₃COC₂H₄OCO— | H | |
| 154 | H | H | C₆H₅—CH₂OCO— | H | |
| 155 | —OCH₃ | H | —NO₂ | H | |
| 156 | H | —NO₂ | H | H | |
| 157 | —CH₃ | H | OH | H | |
| 158 | —Cl | H | CH₃SO₂— | H | |
| 159 | —NO₂ | H | H | H | |
| 160 | —OCH₃ | H | H | H | |
| 161 | H | —OCH₃ | —COCH₃ | H | |
| 162 | H | H | —OCH₃ | H | |
| 163 | —NO₂ | H | H₂NSO₂— | H | |
| 164 | " | H | " | H | |
| 165 | —OH | H | H | H | |
| 166 | H | —CN | H | NCC₂H₄NHSO₂ | |
| 167 | —Cl | H | —OC₂H₅ | Cl | |
| 168 | H | H | H | H | |
| 169 | —Cl | H | —COOC₂H₅ | H | |
| 170 | H | H | —CF₃ | H | |
| 171 | H | H₂NSO₂— | H | H | |
| 172 | H | " | " | H | |
| 173 | H₂NSO₂— | —CH₃ | H | —CH₃ | |
| 174 | " | H | H | —Cl | |
| 175 | H₅C₂NHSO₂ | H₃CNHSO₂— | H | H | |
| 176 | H | H₂NSO₂— | —Cl | H | |
| 177 | —Cl | H | H | NCC₂H₄NHSO₂— | |
| 178 | —Cl | H | —Cl | ClC₂H₄NHSO₂— | |
| 179 | —CH₃ | H | H | —Cl | |
| 180 | H₅C₂OC₂H₄NHSO₂— | H | H | H | |
| 181 | H | morpholino—N—SO₂— | H | H | |
| 182 | H | H | H | —CH₃ | |
| 183 | H | C₆H₁₁—NH—SO₂— | H | H | |
| 184 | —Cl | C₆H₅—CH₂—NHSO₂— | C₆H₅—NHSO₂— | H | |

-continued

|  | A | B1 | B2 | B3 |
|---|---|---|---|---|
| | A₂ A₁ B₁ B₂ | | | |
| | A₃—⟨ ⟩—N=N—C=C—C=O | | | |
| | A₄ A₅ OH N—B₃ | | | |

| No. | | | | |
|---|---|---|---|---|
| 185 | H | H | ⟨phenyl⟩N(CH₃)SO₂— | H |
| 186 | H | H | Cl—⟨phenyl⟩—NHSO₂— | H |
| 187 | —Cl | —OSO₂CH₂Cl | —Cl | H |
| 188 | H | H | NC—C₂H₄SO₂O— | H |
| 189 | H₅C₂SO₂O | H | H₅C₂OC₂H₄SO₂O— | —OCH₃ |
| 190 | H | —Cl | H | H |
| 191 | —CH₃ | CH₃SO₂O— | | —CH₃ |
| 192 | H | —Cl | (CH₃)₂CHCH₂SO₂O— | H |
| 193 | H | ⟨cyclohexyl⟩—SO₂O— | H | H |
| 194 | H | H | CH₃OCO— | H |
| 195 | —NO₂ | H | —NO₂ | H |
| 196 | H | H | —CHO | H |
| 197 | —NO₂ | H | H₃CSO₂— | H |
| 198 | —CN | H | —NO₂ | H |
| 199 | " | H | " | H |
| 200 | —NO₂ | H | —CH₃SO₂— | H |
| 201 | H | H | —NO₂ | H |
| 202 | —Cl | H | " | H |
| 203 | —Br | H | " | H |
| 204 | —SO₂CH₃ | H | " | H |
| 205 | —SO₂C₂H₅ | H | " | H |
| 206 | H | H | —Cl | H |
| 207 | —Cl | H | —Cl | H |
| 208 | —CN | H | —NO₂ | H |
| 209 | —NO₂ | H | " | H |
| 210 | —COOCH₃ | H | " | H |
| 211 | —Cl | H | " | H |
| 212 | —Br | H | " | H |
| 213 | —CN | H | " | H |
| 214 | —NO₂ | H | —Cl | H |
| 215 | CH₃OCO— | H | H | H |
| 216 | H | H | CH₃OCO— | H |
| 217 | H | H | CH₃CO— | H |
| 218 | H | H | C₂H₅OOC | H |
| 219 | —NO₂ | H | H₃CSO₂— | H |
| 220 | —Cl | H | H | —Cl |
| 221 | H | H | —CF₃ | H |
| 222 | H₂NSO₂— | H | —CH₃ | H |
| 223 | —Cl | H₃CSO₂— | —Cl | H |
| 224 | —CH₃ | CH₃SO₂O— | H | —CH₃ |
| 225 | —Cl | H | —NO₂ | H |
| 226 | H | H | —Cl | H |
| 227 | H | —Cl | —Cl | H |
| 228 | H | H | CH₃CO— | H |
| 229 | H | H | CH₃OOC— | H |
| 230 | H | H | —NO₂ | H |
| 231 | H₃C—⟨phenyl⟩—CO— | H | " | H |
| 232 | H | H | H | ⟨phenyl⟩—CO— |
| 233 | —Cl | H | CH₃SO₂— | H |
| 234 | —Cl | H | —NO₂ | H |
| 235 | H | H | (CH₃)₂NSO₂— | H |
| 236 | H | H | —OCH₃ | H |
| 237 | —Br | H | —NO₂ | H |
| 238 | —NO₂ | H | H | H |
| 239 | CH₃SO₂O— | H | H | H |
| 240 | ClC₂H₄SO₂O— | H | H | H |
| 241 | H₉C₄SO₂O— | H | —CH₃ | H |
| 242 | H₅C₂SO₂O— | H | H | —CH₃ |
| 243 | H | H₃CSO₂O— | H | H |
| 244 | H | H₅C₂SO₂O— | H | H |
| 245 | H₆C₅SO₂O— | H | H | H |
| 246 | NCC₂H₄SO₂O— | H | H | H |
| 247 | H | H₉C₄SC₂O— | H | H |
| 248 | H₅C₆CH₂SO₂O— | H | H | H |
| 249 | H | H | H₃CSO₂O— | H |
| 250 | H | H | H₅C₂OC₂H₄SO₂O— | H |
| 251 | H | H | H₇C₃SO₂O— | H |

-continued

[Structure: diazo compound with positions A1-A5 on left ring and B1, B2, B3 on right pyridone ring with OH and =O groups]

| # | A1, A2, A3, A4, A5 | B1 | B2 | B3 |
|---|---|---|---|---|
| 252 | H | H | (cyclohexyl)-SO₂O— | H |
| 253 | —CH₃ | H | H₃CSO₂O— | H |
| 254 | H | —OCH₃ | " | H |
| 255 | H | H₇C₃SO₂O— | H | H |
| 256 | —Cl | H | H | H |
| 257 | (2-Cl-phenyl)-SO₂O— | —CH₃ | H | H |
| 258 | ClCH₂SO₂O— | —CH₃ | H | H |
| 259 | H₃CCHClSO₂O— | tert-H₉C₄SO₂O— | H | H |
| 260 | —CH₃ | n-C₆H₁₃SO₂O— | H | H |
| 261 | —Cl | H | H | H |
| 262 | H | (cyclohexyl)-SO₂O— | C₆H₅CH₂SO₂O— | H |
| 263 | H | —CH₃ | C₆H₅SO₂O— | —CH₃ |
| 264 | —OCH₃ | " | (4-Cl-phenyl)-SO₂O— | H |
| 265 | H | —Cl | (4-H₃CO-phenyl)— | H |
| 266 | (H₃C)₂NSO₂O— | H | H | H |
| 267 | " | H | H | —Cl |
| 268 | (H₉C₄)₂NSO₂O— | H | H | H |
| 269 | H₂NSO₂O— | H | H | H |
| 270 | H₇C₃NHSO₂O— | H | H | H |
| 271 | H | (H₃C)₂NSO₂O— | H | H |
| 272 | H | (H₉C₄)₂NSO₂O— | H | H |
| 273 | H | (morpholinyl)N—SO₂O— | H | H |
| 274 | H | (piperidinyl)N—SO₂O— | H | H |
| 275 | H | (phenyl)-NHSO₂O— | H | H |
| 276 | H | (phenyl)-N(CH₃)SO₂O— | H | H |
| 277 | H | —CH₃ | (H₃C)₂NSO₂O— | —CH₃ |
| 278 | H | H | (H₃C)₂NSO₂O— | H |
| 279 | H | —CH₃ | (H₃C)₂NSO₂O— | H |
| 280 | (3-H₃C-phenyl)-NHSO₂O— | H | —CH₃ | —CH₃ |
| 281 | H | (phenyl)-N(C₂H₅)SO₂O— | H | H |
| 282 | H | H | (4-H₃CO-phenyl)-NHSO₂O— | H |
| 283 | (4-H₃C-phenyl)-NHSO₂O— | —CH₃ | H | H |
| 284 | (2-CH₃-phenyl)-NHSO₂O— | —CH₃ | —CH₃ | H |
| 285 | (4-Cl-phenyl)-NHSO₂O— | H | —OCH₃ | H |
| 286 | (phenyl)-NHSO₂O— | H | H | —Cl |
| 287 | H | H₅C₆CH₂NHSO₂O— | H | —CH₃ |
| 288 | —CH₃ | H₅C₆(C₆H₁₃)NSO₂O— | —CH₃ | H |
| 289 | —CH₃ | ClC₂H₄NHSO₂O— | H | —CH₃ |
| 290 | H | H₅C₂OC₂H₄NHSO₂O— | —CH₃ | H |
| 291 | —Cl | H₇C₃NHSO₂O— | —Cl | H |

-continued

Structure: A2, A1 on benzene ring with A3, A4, A5; connected via N=N to pyridone with B1, B2, B3 (N-substituent), OH and =O groups.

| No. | A1-A5 positions | B1 | B2 | B3 |
|---|---|---|---|---|
| 292 | H | —CH3 | H9C4NHSO2O— | H |
| 293 | H | " | (H7C3)2NSO2O— | H |
| 294 | H | —OCH3 | " | H |
| 295 | —OCH3 | H | (H9C4)2NSO2O— | H |
| 296 | H | —Cl | " | H |
| 297 | H | H | H7C3NHSO2O— | H |
| 298 | H | H5C6(CH3)NSO2O— | H | H |
| 299 | H | (H3C)2NSO2O— | " | H |
| 300 | H | (H2C-CH2)N—SO2O— (aziridine) | H | H |
| 301 | —NO2 | H | morpholine-N—SO2O— | H |
| 302 | H | cyclohexyl-NHSO2O— | H | H |
| 303 | H | NC—C2H4SO2O— | H | H |
| 304 | NCC2H4SO2O— | H | H | —Cl |
| 305 | morpholine-N—SO2O— | H | OCH3 | H |
| 306 | H | H | C6H5SO2O— | H |
| 307 | H | H | H3CO-C6H4-SO2O— | H |
| 308 | H | CH3SO2O— | H | H |
| 309 | H | " | —Cl | H |
| 310 | H | H5C6CH2SO2O— | —CH3 | H |
| 311 | —CH3 | CH3SO2O— | " | H |
| 312 | CH3SO2O— | H | H | —CH3 |
| 313 | H | —Cl | H5C2OC2H4SO2O— | H |
| 314 | H | H | C2H5OOC— | H |
| 315 | —Cl | H3CHNSO2O— | —NO2 | H |
| 316 | H | —Cl | H | H |
| 317 | H | —Cl | —Cl | H |
| 318 | H | —Cl | —Cl | H |
| 319 | H | —Cl | —Cl | H |
| 320 | H | —Cl | —Cl | H |
| 321 | H | H | H2NSO2— | H |
| 322 | H | H | " | H |
| 323 | H | H | " | H |
| 324 | H | H | H | H |
| 325 | H | (CH3)2NSO2— | H | H |
| 326 | H | " | H | H |
| 327 | H | " | H | H |
| 328 | H | " | H | H |
| 329 | H | H7C3SO2O— | H | H |
| 330 | H | " | H | H |
| 331 | H | " | H | H |
| 332 | H | " | H | H |
| 333 | H | H | C2H5HNSO2— | H |
| 334 | H | H | " | —OCH3 |
| 335 | H | H | C2H5OC2H4SO2— | H |
| 336 | H | H | 3-OCH3-C6H4-HNSO2— | H |
| 337 | CH3NHSO2— | H | —CH3 | H |
| 338 | CH3NHSO2— | H | H | —CH3 |
| 339 | " | H | —CH3 | " |
| 340 | " | H | —CH3 | H |
| 341 | —Br | H | —NO2 | H |
| 342 | H | H | H | H |
| 343 | H | —NO2 | H | H |
| 344 | —NO2 | —NO2 | —NO2 | H |
| 345 | —CN | H | H | H |
| 346 | H | —NO2 | —NO2 | H |
| 347 | H | " | H | H |
| 348 | H | " | H | H |
| 349 | H | " | H | H |
| 350 | H | " | H | H |
| 351 | H | " | —NO2 | H |
| 352 | H | H | " | H |
| 353 | —NO2 | H | —NO2 | H |
| 354 | —Cl | H | —NO2 | H |
| 355 | H | H | CH3OCO— | H |

-continued

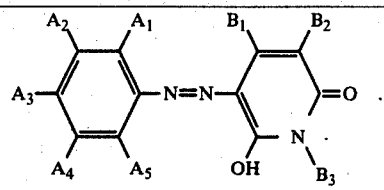

| No. | A1 | A2 | A3 | A4 | A5 | B1 | B2 | B3 |
|---|---|---|---|---|---|---|---|---|
| 356 | —Cl | | | | | H | —NO₂ | H |
| 357 | —NO₂ | | | | | H | CH₃SO₂— | H |
| 358 | —CN | | | | | H | H | —Cl |
| 359 | —Cl | | | | | H | CH₃SO₂— | H |
| 360 | H | | | | | H | H₅C₆CONH— | H |
| 361 | —Br | | | | | H | H₅C₆SO₂NH— | H |
| 361a | H | | | | | H | H₅C₂OCONH— | H |
| 361b | H | | | | | H | H₅C₆SO₂— | H |
| 361c | —Br | | | | | H | CH₃SO₂NH— | H |
| 361d | H | | | | | H | C₂H₅SO₂NH— | H |
| 361e | —Cl | | | | | H | —NO₂ | H |
| 361f | H | | | | | H | " | H |
| 361g | —NO₂ | | | | | H | " | H |
| 361h | H | | | | | —NO₂ | " | H |
| 361i | H | | | | | " | " | H |
| 361j | H | | | | | H | —Cl | H |
| 361k | —Cl | | | | | H | —NO₂ | H |
| 361l | —Cl | | | | | H | H | —Cl |
| 361m | H | | | | | H | —NO₂ | H |
| 361n | H | | | | | —NO₂ | H | H |
| 361o | H | | | | | Cl | Cl | H |
| 361p | H | | | | | Cl | Cl | H |
| 361q | H | | | | | —NO₂ | H | H |

| Examp. No. | A5 | B1 | B2 | B3 |
|---|---|---|---|---|
| 8 | H | —CH₃ | —CN | —CH₂CH₂COOCH₃ |
| 9 | H | " | " | —CH₂CH₂OH |
| 10 | H | " | " | " |
| 11 | H | —C₃H₇ | " | " |
| 12 | H | —C₆H₅ | " | —C₂H₄CN |
| 13 | H | —CH₃ | " | —C₂H₄Cl |
| 14 | H | " | " | " |
| 15 | —CN | —C₂H₅ | —COCH₃ | " |
| 16 | H | —CH₃ | —CN | —CH₂CH(OH)CH₃ |
| 17 | H | " | " | —CH₂CH₂OCOCH₃ |
| 18 | H | " | " | —CH₂CH₂OCOC₆H₅ |
| 19 | H | " | " | —CH₂CH₂OCOC₂H₅ |
| 20 | H | " | " | —CH₂CH₂OCOC₃H₇ |
| 21 | H | " | " | —CH₂CH₂OCOOC₂H₅ |
| 22 | H | " | " | —CH₂CH₂OCOOC₆H₅ |
| 23 | H | " | " | —CH₂CH₂COOCH₃ |
| 24 | H | " | " | —CH₂CH₂OCOCH=CH₂ |
| 25 | H | " | " | —CH₂CH₂COOC₆H₅ |
| 26 | —Cl | " | " | —C₂H₄OH |
| 27 | H | " | " | " |
| 28 | H | " | " | —CH₂CH(OH)CH₂OCH₃ |
| 29 | H | " | " | —CH₂CH₂COCH₃ |
| 30 | H | " | " | " |
| 31 | H | " | —COCH₃ | " |
| 32 | H | " | " | " |
| 33 | H | " | —CN | —C₂H₅ |
| 34 | —Cl | " | " | " |
| 35 | H | " | " | " |
| 36 | H | " | " | —CH₂CH₂OCOCH₃ |
| 37 | H | " | " | —CH₂CH₂CN |
| 38 | H | " | " | —CH₂CH₂Cl |
| 39 | H | " | " | —C₃H₆OCH₃ |
| 40 | H | " | —COCH₃ | " |
| 41 | H | " | —SO₂CH₃ | " |
| 42 | H | " | —SO₂C₂H₅ | " |
| 43 | H | " | —CN | " |
| 44 | H | " | " | " |
| 45 | H | " | " | " |
| 46 | H | " | " | " |
| 47 | H | " | " | —C₂H₄COC₆H₅ |
| 48 | H | " | " | " |
| 49 | H | " | " | " |
| 50 | H | " | " | " |
| 51 | H | " | " | —C₂H₄SO₂CH=CH₂ |
| 52 | H | " | " | —CH₂-(cyclopentyl-SO₂) |
| 53 | H | " | " | —C₂H₄OC₂H₄CN |
| 54 | H | " | " | —NHCOC₂H₅ |
| 55 | H | " | " | —NHC₆H₅ |
| 56 | H | " | " | —NH-C₆H₁₁ |
| 57 | H | " | " | —C₂H₄OC₂H₄COOCH₃ |

-continued

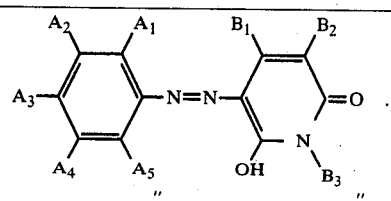

| | $A_1$ | $A_2, A_3, A_4, A_5$ | $B_1$ | $B_2$ | $B_3$ |
|---|---|---|---|---|---|
| 58 | H | " | | | 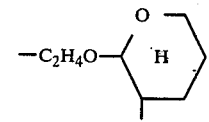 |
| 59 | H | " | | |  |
| 60 | H | " | $-C_2H_5$ | " | $-C_2H_4OSO_2C_2H_5$ |
| 61 | H | " | $-C_3H_7$ | " | " |
| 62 | H | " | " | " | $-C_2H_4CONH_2$ |
| 63 | H | " | " | " | $-C_2H_4COOC_2H_4OCOCH_3$ |
| 64 | H | " | " | " | $-C_2H_4OC_2H_4OC_6H_5$ |
| 65 | H | " | " | " | $-C_2H_4OC_2H_4OCONHC_6H_5$ |
| 66 | H | " | $-CH_3$ | " | " |
| 67 | H | " | " | " | " |
| 68 | H | " | " | " | $-C_2H_4OC_2H_4OCH_3$ |
| 69 | H | " | " | " | $-C_2H_4COOCH_2CN$ |
| 70 | H | " | " | " | $-CH_2CHOHCH_2CN$ |
| 71 | H | " | " | " | $-CH_2SO_2C_2H_4SC_6H_5$ |
| 72 | H | " | " | " | $-C_2H_4OCH_3$ |
| 73 | H | " | " | " | $-C_2H_4SO_2OC_6H_5$ |
| 74 | H | " | " | " | $-C_3H_6OCH_3$ |
| 75 | H | " | " | " | (trimethylcyclohexyl group) |
| 76 | H | " | " | " | $-C_3H_6OCH_3$ |
| 77 | H | " | " | " | (cyclohexyl) |
| 78 | H | " | " | " | $-C_2H_4OH$ |
| 79 | H | " | $-C_6H_5$ | " | " |
| 80 | H | " | " | " | " |
| 81 | H | " | " | " | " |
| 82 | H | " | " | " | " |
| 83 | H | " | " | " | $-CH_3$ |
| 84 | H | " | " | " | " |
| 85 | H | " | " | " | " |
| 86 | H | " | " | " | " |
| 87 | H | " | " | " | " |
| 88 | H | " | " | $-COCH_3$ | " |
| 89 | H | " | " | $-COC_6H_5$ | " |
| 90 | H | " | " | $-COCH_3$ | $-C_4H_9$ |
| 91 | H | " | $-CH_3$ | $-CN$ | $-C_2H_4CN$ |
| 92 | H | " | " | " | " |
| 93 | H | " | " | " | " |
| 94 | H | " | " | " | $-C_2H_4OCOCH_3$ |
| 95 | H | " | " | " | " |
| 96 | H | " | " | " | $-CH_3$ |
| 97 | H | " | " | " | " |
| 98 | H | " | " | " | $-C_2H_4OH$ |
| 99 | H | " | " | " | $-C_3H_6OCH_3$ |
| 100 | H | " | " | " | $-CH_3$ |
| 101 | H | " | " | " | $-C_2H_4OH$ |
| 102 | H | " | " | " | $-C_3H_6OCH_3$ |
| 103 | H | " | " | " | $-CH_3$ |
| 104 | H | " | " | " | $-C_2H_4OH$ |
| 105 | H | " | " | " | $-C_3H_6OCH_3$ |
| 106 | H | " | " | " | $-CH_3$ |
| 107 | H | " | " | " | $-C_2H_4OH$ |
| 108 | H | " | " | " | $-C_3H_6OCH_3$ |
| 109 | H | " | " | " | $-C_2H_4OH$ |
| 110 | H | " | " | " | $-C_3H_6OCH_3$ |
| 111 | H | " | " | " | $-CH_3$ |
| 112 | H | 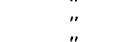 (4-CH₃-C₆H₄) | " | " | $-C_2H_5$ |
| 113 | H | 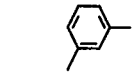 (3-CH₃O-C₆H₄) 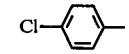 (4-Cl-C₆H₄) | " | " | $-CH_3$ |

-continued

Structure: Ar-N=N-pyridone with substituents A1-A5 on phenyl ring and B1, B2, B3 on pyridone ring (with OH and =O groups).

| No. | A | B₁ | B₂ | B₃ |
|---|---|---|---|---|
| 114 | H | 3-nitrophenyl | " | " |
| 115 | H | 3-pyridyl | —CN | —CH₂—CH(CH₃)CH₃ |
| 116 | H | 2-thienyl | " | —C₂H₄Cl |
| 117 | H | " | " | —C₃H₆OC₂H₅ |
| 118 | H | 2-furyl | " | —CH₂CHOHCH₃ |
| 119 | H | 4-(CH₃CONH)phenyl | " | —C₂H₅ |
| 120 | H | —C₃H₇ | " | —C₂H₄OH |
| 121 | H | —CH₃ | " | " |
| 122 | H | " | " | " |
| 123 | H | —C₂H₅ | " | —C₂H₄CN |
| 124 | H | —CH₃ | " | —C₂H₄Cl |
| 125 | H | " | " | cyclohexyl |
| 126 | —Cl | 4-methoxyphenyl | " | —CH₃ |
| 127 | H | —CH₃ | —COCH₃ | —C₃H₆OCH₃ |
| 128 | H | " | —COOC₂H₅ | —C₂H₄OH |
| 129 | H | " | " | —C₂H₄OCONHC₆H₅ |
| 130 | H | " | " | —C₂H₄COOCH₂CN |
| 131 | H | " | —CN | —C₃H₆OCH₃ |
| 132 | H | " | " | —CH₃ |
| 133 | H | —C₆H₄—CH₃ | —COC₆H₅ | —C₂H₅ |
| 134 | H | —CH₃ | " | " |
| 135 | H | " | —CN | —C₂H₄SO₂C₂H₄SC₆H₅ |
| 136 | H | —CH₃ | —CN | —CH₂CHOHCH₂CN |
| 137 | —NO₂ | —CH₃ | —CH₃ | —C₂H₄OHCH₂OC₆H₅ |
| 138 | H | —C₆H₅ | —CN | —C₂H₄COOCH₂CN |
| 139 | H | " | " | —C₂H₄OC₂H₄OCH₃ |
| 140 | H | 3-(methylthio)pyrazinyl | —COCH₃ | —C₂H₄OCOC₂H₄OCH₃ |
| 141 | H | —CH₃ | —COC₆H₅ | —C₂H₄—O—(3-chloro-tetrahydrofuryl) |
| 142 | —NO₂ | cyclohexyl | —CN | —C₂H₄OCOCH=CH₂ |
| 143 | H | 3-chloro-4-methylphenyl | —CONHC₂H₅ | —C₂H₄OCOCH₃ |
| 144 | H | 4-cyanophenyl | —CON(CH₃)₂ | —C₂H₄OCOC₂H₅ |
| 145 | H | —C₃H₇ | —CN | —C₂H₄COOC₂H₅ |
| 146 | H | —CH₃ | " | —C₂H₄OCOC₆H₅ |
| 147 | H | " | —COCH₃ | " |
| 148 | H | " | —CN | —CH₃ |
| 149 | H | " | " | —C₂H₄SO₂OC₆H₅ |
| 150 | —Cl | " | —COCH₃ | —C₂H₄OC₂H₄OCONHC₆H₅ |
| 151 | H | " | —CN | —C₂H₄OC₂H₄OC₆H₅ |
| 152 | H | —C₂H₅ | —SO₂CH₃ | —C₂H₄COOC₂H₄OCOCH₃ |
| 153 | H | —CH₃ | —CN | —C₂H₄OSO₂C₆H₅ |
| 154 | H | " | —CN | " |
| 155 | H | " | —CON(CH₃)₂ | " |

4,140,684

-continued $$\underset{A_4}{\overset{A_2}{\underset{A_3}{\bigcirc}}}\overset{A_1}{\underset{A_5}{\bigcirc}}-N=N-\underset{OH}{\overset{B_1}{\underset{N-B_3}{\bigcirc}}}\overset{B_2}{=O}$$

| No. | A | A' | B₁ | B₂ | B₃ |
|---|---|---|---|---|---|
| 156 | H | " | —CO—(3-cyanopiperidinyl) | | —C₂H₄CONH₂ |
| 157 | H | | —C₃H₇ | —CN | —C₂H₄OCONHC₂H₅ |
| 158 | H | | (3-pyridyl)CH₂— | " | —C₂H₄OC₂H₄OCOCH₃ |
| 159 | —Cl | | H₃CO—C₆H₄—CH₂— | —SO₂C₂H₅ | —C₂H₄OC₂H₄COOCH₃ |
| 160 | H | | —C₆H₅ | —COOC₆H₅ | —C₂H₄OSO₂C₆H₅ |
| 161 | H | | —C₄H₉ | —SO₂—C₆H₅ | —C₂H₄OSO₂CH₃ |
| 162 | H | | —C₃H₇ | —OC₂H₅ | —C₂H₄CONH₂ |
| 163 | H | | —CH₃ | —CN | 3,3,5-trimethylcyclohexyl |
| 164 | H | | —C₆H₅ | " | cyclohexyl |
| 165 | H | | —C₃H₇ | " | —C₂H₄COC₆H₅ |
| 166 | H | | —CH₃ | " | —C₂H₄COCH₃ |
| 167 | H | | " | " | CH₂CHOHCH₂OCH₃ |
| 168 | H | | " | " | —C₂H₄SO₂CH=CH₃ |
| 169 | H | | " | " | tetrahydrothiophene-SO₂ |
| 170 | H | | " | " | —C₂H₄OC₂H₄CN |
| 171 | H | | —C₆H₅ | " | —CH₂CHOHCH₂Cl |
| 172 | H | | " | " | —CH₂CHOHCH₂CN |
| 173 | H | | —CH₃ | " | —CH₂CHClCH₂CN |
| 174 | H | | " | " | —CH₂CH₂CH₂OH |
| 175 | H | | —C₆H₅ | —COCH₃ | —CH₂C₆H₅ |
| 176 | —CH₃ | | —CH₃ | " | —C₂H₄OCONHC₆H₅ |
| 177 | H | | " | " | —CH₃ |
| 178 | H | | —CH₃ | —CN | iso-C₃H₇ |
| 179 | H | | " | " | —C₂H₄OH |
| 180 | H | | " | " | —C₂H₄COCH₃ |
| 181 | —Cl | | " | " | —C₂H₄Cl |
| 182 | H | | " | " | —C₂H₄CN |
| 183 | H | | " | " | —C₂H₄OCOC₂H₅ |
| 184 | H | | " | " | —C₂H₄OCOC₂H₅ |
| 185 | H | | " | " | —C₂H₄OC₂H₅ |
| 186 | H | | " | " | —C₃H₆OCH₃ |
| 187 | H | | " | " | n-C₄H₉ |
| 188 | H | | " | " | —C₂H₅ |
| 189 | H | | —C₂H₅ | " | n-C₃H₇ |
| 190 | H | | —CH₃ | —COCH₃ | —CH₃ |
| 191 | H | | —C₃H₇ | —CN | tert.—C₄H₉ |
| 192 | H | | —C₆H₅ | " | —CH₃ |
| 193 | —CH₃ | | —CH₃ | " | " |
| 194 | H | | —C₆H₅ | " | —C₃H₆OCH₃ |
| 195 | H | | —CH₃ | " | —CH₃ |
| 196 | H | | —C₆H₅ | —COCH₃ | —C₂H₅ |
| 197 | H | | —CH₃ | —CN | —C₂H₄OC₂H₅ |
| 198 | Br | | " | " | —C₂H₄CN |
| 199 | H | | —C₂H₅ | —COCH₃ | cyclohexyl |
| 200 | H | | —C₂H₅ | —CN | cyclohexyl |
| 201 | H | | —CH₃ | " | —C₂H₄CON(CH₃)₂ |
| 202 | H | | —CH₂CH₂OH | —CONHC₆H₅ | —C₂H₄CO-cyclohexyl |
| 203 | H | | —CH₂CH₂OCH₃ | —CN | —CH₂-cyclohexyl |
| 204 | H | | —CH₂CH₂CN | —CON(CH₃)C₆H₅ | —C₂H₄SO₂CH₃ |

-continued

Structure: A phenyl ring with substituents A₁, A₂, A₃, A₄, A₅ connected via N=N azo group to a pyridone ring with B₁, B₂ substituents, OH group, and N-B₃.

| No. | A | B₁ (substituent) | B₂ | B₃ |
|-----|---|------|-----|-----|
| 205 | H | —CH₂CH₂CONH₂ | —CO—C₆H₁₁ (cyclohexyl) | —C₂H₄SO₂—C₆H₁₁ |
| 206 | H | —CH₃ | —COCH₂C₆H₅ | —C₂H₄SO₂C₆H₅ |
| 207 | H | " | (2-thienyl-CO—) | C₂H₄SO₂CH₂C₆H₅ |
| 208 | H | " | —CO—N(CH₃)₂ | —C₂H₄OSO₂C₆H₅ |
| 209 | H | —C₆H₅ | —CONH₂ | —C₂H₄OSO₂—C₆H₁₁ |
| 210 | H | —C₃H₆OCH₃ | —CO—C₆H₄—Cl | —CH₃ |
| 211 | —Cl | —C₂H₄Cl | —SO₂NH₂ | —C₂H₄OH |
| 212 | —NO₂ | (2-methylnaphthyl) | —SO₂NHC₃H₇ | —C₂H₄CN |
| 213 | —Br | (methyl naphthyl) | —SO₂N(CH₃)₂ | —CH₃ |
| 214 | H | (methoxy/ethoxy naphthyl with OC₂H₅) | —SO₂N(CH₃)C₆H₅ | —C₄H₉ |
| 215 | H | H₃C—C₆H₁₀— (4-methylcyclohexyl) | —CN | —C₃H₇ |
| 216 | H | (2-aminophenyl with N=C imine, NH) | " | —CH₃ |
| 217 | H | (3-methylthienyl, CH₃) | —COCH₃ | " |
| 218 | H | H₃CSO₂—(benzothiazol-2-yl) | —COOC₂H₅ | —CH₃ |
| 219 | H | H₃CO—(benzothiazol-2-yl) | —CN | " |
| 220 | H | H₃CCO—C₆H₄— | " | —C₂H₅ |
| 221 | H | (H₃C)₂N—C₆H₄— | —CON(CH₃)₂ | —CH₃ |
| 222 | H | (H₃C)₂NSO₂—C₆H₄— | —CN | " |
| 223 | H | H₃COOC—C₆H₁₀— | " | " |
| 224 | H | HO—C₆H₄— | " | " |
| 225 | H | —CH₃ | —COOC₂H₅ | —C₂H₅ |
| 226 | H | " | COOCH₂C₆H₅ | —C₃H₆OCH₃ |
| 227 | H | " | —CN | —N(CH₃)₂ |
| 228 | H | " | " | —N(C₂H₅)₂ |
| 229 | H | " | " | —N(CH₂CH₂OH)₂ |
| 230 | H | " | " | —N(CH₂CH₂CN)₂ |
| 231 | H | " | —COCH₃ | —N(CH₂CH₂Cl)₂ |
| 232 | H | " | —CN | —N(CH₂CH₂OCOCH₃)₂ |
| 233 | H | " | " | —N(piperidinyl) |
| 234 | H | " | " | —N(morpholinyl) |

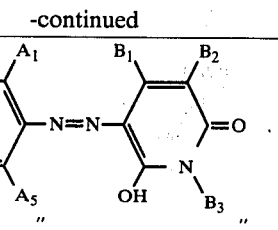

| No. | A | B₁ | B₂ | B₃ |
|---|---|---|---|---|
| 235 | H | " | " | 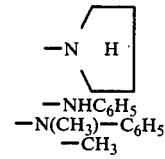 |
| 236 | H | " | " | —NHC₆H₅ |
| 237 | —Cl | —CH₃ | —CN | —N(CH₃)—C₆H₅ |
| 238 | 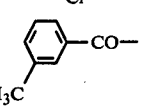 | " | " | —CH₃ |
| 239 | H | —C₆H₅ | " | " |
| 240 | H | " | " | " |
| 241 | H | " | " | —C₄H₉ |
| 242 | H | " | —COCH₃ | —CH₃ |
| 243 | H | " | —COOC₂H₅ | " |
| 244 | —CH₃ | " | —SO₂CH₃ | " |
| 245 | H | " | " | —N(CH₃)₂ |
| 246 | H | " | —CN | —CH₂CH₂OC₂H₅ |
| 247 | H | " | " | —CH₂C₆H₅ |
| 248 | H | " | " | —C₃H₆OCH₃ |
| 249 | H | " | " | —N(CH₂CH₂Cl)₂ |
| 250 | H | " | " | —C₃H₆OCH₃ |
| 251 | H | " | " | —N(CH₂CH₂OCOCH₃)₂ |
| 252 | H | " | " | —C₂H₅ |
| 253 | —CH₃ | " | " | " |
| 254 | H | " | " | " |
| 255 | H | " | " | " |
| 256 | H | " | " | " |
| 257 | H | " | " | —N(CH₃)₂ |
| 258 | H | —CH₃ | —CN | —N(CH₃)₂ |
| 259 | H | " | " | " |
| 260 | H | " | " | " |
| 261 | —Cl | " | " | " |
| 262 | H | " | " | —CH₃ |
| 263 | H | " | " | " |
| 264 | H | " | " | " |
| 265 | H | " | " | " |
| 266 | H | " | " | —CH₂CH₂OH |
| 267 | H | " | " | " |
| 268 | H | —C₂H₅ | " | " |
| 269 | H | " | " | " |
| 270 | H | " | " | " |
| 271 | H | " | " | —C₄H₉ |
| 272 | H | " | " | " |
| 273 | H | " | " | —CH₃ |
| 274 | H | —CH₃ | —COCH₃ | " |
| 275 | H | " | " | " |
| 276 | H | " | " | " |
| 277 | H | " | " | " |
| 278 | H | —CH₃ | —COOC₃H₇ | —CH₃ |
| 279 | H | " | " | " |
| 280 | H | " | " | " |
| 281 | H | " | —CN | —N(CH₃)₂ |
| 282 | H | " | " | " |
| 283 | H | " | " | 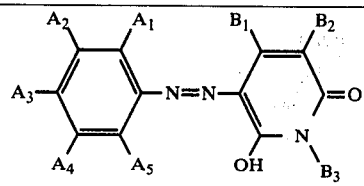 |
| 284 | H | " | —COCH₃ | —C₃H₆OCH₃ |
| 285 | H | " | " | " |
| 286 | H | —C₆H₅ | —CN | " |
| 287 | H | " | " | " |
| 288 | H | " | " | " |
| 289 | H | " | " | " |
| 290 | H | " | —COCH₃ | " |
| 291 | H | " | " | —C₂H₄OH |
| 292 | H | " | " | " |
| 293 | H | " | " | " |
| 294 | H | " | " | " |
| 295 | H | " | —CN | " |
| 296 | H | " | " | " |
| 297 | H | —C₆H₅ | —CN | —N(C₂H₅)₂ |
| 298 | H | " | " | " |
| 299 | H | —CH₃H₇ | —CN | —C₂H₄OH |
| 300 | H | —CH₃ | —CN | —CH₃ |
| 301 | H | " | " | " |
| 302 | H | " | —COCH₃ | —C₃H₆OCH₃ |
| 303 | H | " | —CN | —C₃H₇ |
| 304 | H | " | " | —N(CH₃)₂ |

-continued

Structure: A₁-A₅ substituted phenyl-N=N- linked to pyridone with B₁, B₂, B₃ substituents, OH, and C=O groups.

| No. | A | (col 3) | B₂ | B₃ |
|---|---|---|---|---|
| 305 | H | " | " | morpholino-N— |
| 306 | H | —C₂H₅ | " | C₆H₅—NH— |
| 307 | H | " | " | pyrrolidino-N— |
| 308 | H | —C₃H₇ | " | —C₃H₇ |
| 309 | H | " | " | —CH₃ |
| 310 | H | —CH₃ | " | —N(C₂H₅)₂ |
| 311 | H | " | " | —N(CH₃)C₆H₅ |
| 312 | H | " | " | —N(CH₂CH₂OH)₂ |
| 313 | H | " | " | —N(CH₂CH₂CN)₂ |
| 314 | H | —C₆H₅ | " | —CH₃ |
| 315 | H | 2-thienyl | " | —N(CH₃)₂ |
| 316 | H | 2-pyridyl | " | —CH₃ |
| 317 | H | —CH₃ | —CN | —C₂H₅ |
| 318 | H | —C₆H₅ | " | —CH₃ |
| 319 | H | —CH₃ | " | —(CH₂)₃OCH₃ |
| 320 | H | —C₆H₅ | " | —N(CH₃)₂ |
| 321 | H | —CH₃ | " | —CH₂CH₂OCH₃ |
| 322 | H | " | " | —NH(CH₂)₃OCH₃ |
| 323 | H | —C₆H₅ | " | —CH₃ |
| 324 | H | —C₆H₅ | " | —NHCH₃ |
| 325 | H | " | " | —NH(CH₃)₂ |
| 326 | H | " | " | —CH₃ |
| 327 | H | —CH₃ | " | —CH(CH₃)₂ |
| 328 | H | " | " | —N(C₂H₅)₂ |
| 329 | H | " | " | —NHCH₂CH₂CN |
| 330 | H | " | " | —CH₂CH₂CH₂CH₃ |
| 331 | H | —C₆H₅ | " | —CH₃ |
| 332 | H | " | " | —N(CH₃)₂ |
| 333 | —OCH₃ | " | " | —CH₃ |
| 334 | H | " | " | —NHCH₃ |
| 335 | —OCH₃ | —CH₃ | " | —N(C₂H₅)₂ |
| 336 | " | " | " | —C₂H₅ |
| 337 | H | " | " | —N(CH₃)₂ |
| 338 | H | —C₆H₅ | —CN | —CH₃ |
| 339 | H | —CH₃ | " | —CH₂CH₂OCH₃ |
| 340 | H | —C₆H₅ | " | —N(CH₃)₂ |
| 341 | H | —CH₃ | " | CH₃COOC₂H₄— |
| 342 | H | —C₆H₅ | " | " |
| 343 | H | " | " | C₂H₅COOC₂H₄— |
| 344 | H | —CH₃ | " | CNCH₂COOC₂H₄— |
| 345 | —CN | " | " | ClCH₂COOC₂H₄— |
| 346 | H | " | " | H₅C₆COOC₂H₄— |
| 347 | H | " | " | H₅C₆CH₂COOC₂H₄— |
| 348 | H | " | " | 4-H₃COH₄C₆COOC₂H₄— |
| 349 | H | " | " | 4-ClH₄C₆COOC₂H₄— |
| 350 | H | " | " | 2,4-Cl₂H₃C₆COOC₃H₄— |
| 351 | H | —C₆H₅ | " | C₃H₇COOC₂H₄— |
| 352 | H | " | " | CH=CHCOOC₂H₄— |
| 353 | H | —CH₃ | " | CH₃COOC₂H₄OCOC₂H₄— |
| 354 | H | —C₃H₇ | " | CH₃COOC₂H₄— |
| 355 | H | —CH₃ | " | C₄H₉COOC₂H₄— |
| 356 | —Cl | —C₂H₅ | " | CH₃COOC₃H₆— |
| 357 | H | " | " | CH₃COOC₂H₄— |
| 358 | H | —C₃H₇ | " | CH₃COOC₂H₄— |
| 359 | H | " | " | C₂H₅COOC₂H₄— |
| 360 | H | —C₆H₅ | " | CH₃COOC₂H₄— |
| 361 | —NO₂ | —CH₂CH₂Cl | —CN | H₅C₆COOC₂H₄— |
| 361a | —Br | —CH₂CH₂Br | " | —CH₃ |
| 361b | " | —CH₂CN | " | " |
| 361c | H | —CH₂OCH₃ | " | " |
| 361d | —NO₂ | —CH₂OC₂H₅ | " | " |
| 361e | H | —CH₃ | " | —C₆H₅ |
| 361f | H | " | " | 4-Cl-C₆H₄— |
| 361g | H | " | " | 4-NO₂-C₆H₄— |

-continued

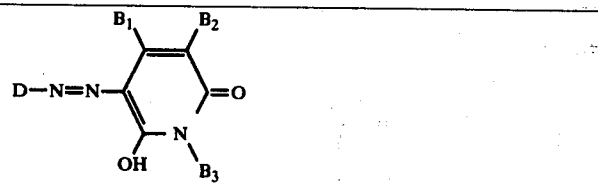

| | | | | |
|---|---|---|---|---|
| 361h | H | " | " | (3-cyanophenyl) |
| 361i | H | " | " | (4-hydroxyphenyl) |
| 361j | H | " | " | (4-methylphenyl) |
| 361k | —NO₂ | " | " | (2-ethoxyphenyl) |
| 361l | H | " | " | (2-trifluoromethylcyclohexyl) |
| 361m | H | " | " | (1-hydroxy-2-methyl-6-bromonaphthyl) |
| 361n | H | " | " | (2-methylphenyl)-NHC₆H₅ |
| 361o | H | " | " | —NHC₆H₅ |
| 361p | H | " | " | " |
| 361q | H | —CH₃ | —CN | —NHC₂H₅ |

The dyes listed in Table 2 are of formula

| Examp. No. | D | $B_1$ | $B_2$ | $B_3$ |
|---|---|---|---|---|
| 362 | 6-Methoxybenzothiazolyl-2 | —CH₃ | —CN | —CH₂CH₂OH |
| 363 | 6-Methylsulphonylbenzothiazolyl-2 | " | " | " |
| 364 | 6-Nitrobenzothiazolyl-2 | " | " | —C₂H₅ |
| 365 | 4-Phenyl-5-nitrothiazolyl-2 | " | " | " |
| 366 | 5-Nitrothiazolyl-2 | " | " | " |
| 367 | 1,3,5-Triazolyl-2 | " | " | —CH₂CH₂CH₂OCH₃ |
| 368 | Imidazolyl-2 | " | " | " |
| 369 | 1-Methyl-5-chlorobenzimidazolyl-7 | " | " | " |
| 370 | 1-phenyl-3-methylpyrazolyl-7 | " | " | —CH₂CH₂OH |
| 371 | 5,6-Dimethoxybenzothiazolyl-2 | 2-Methylphenyl | " | —CH₃ |
| 372 | 3-Methylthiadiazolyl-5 | —C₆H₅ | " | " |
| 373 | 2-Acetyl-4-nitrothienyl-5 | —CH₃ | —COCH₃ | " |
| 374 | 1-Methyl-4-cyanopyrazolyl-5 | " | —CN | —CH₂CH₂CH₂OCH₃ |
| 375 | 4-Methyl-5-cyanothiazolyl-2 | —C₂H₅ | " | —CH₃ |
| 376 | 5-Ethylsulphonylthiazolyl-2 | —CH₃ | " | " |
| 377 | 1-Methyl-4-nitroimidazolyl-5 | " | " | —C₂H₅ |
| 378 | 6-Methoxybenzothniazolyl-2 | " | " | —CH₂CH₂OH |
| 379 | 6-β-Cyanoethylsulfonyl-benzothiazolyl-2 | —C₆H₅ | " | " |
| 380 | 6-Aminosulphonylbenzothia- | " | " | —CH₃ |

-continued

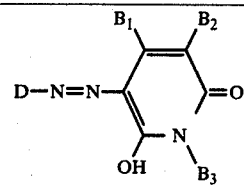

| Examp. No. | D | B₁ | B₂ | B₃ |
|---|---|---|---|---|
| | zolyl-2 | | | |
| 381 | 4-Nitrothiazolyl-5 | " | " | —CH₂CH₂CH₂OCH₃ |
| 382 | 2-Acetyl-4-nitrothienyl-5 | " | " | —CH₃ |
| 383 | 5,6-Dimethoxybenzothiazolyl-2 | 3-Methoxyphenyl | " | " |
| 384 | 4-Phenylazophenyl | —CH₃ | " | —CH₂CH₂COC₆H₅ |
| 385 | 2-Methoxy-4-(4'-nitrophenylazo)-phenyl | " | " | " |
| 386 | 4-Phenylazonaphthyl | " | " | —CH₂CH₂CN |
| 387 | 2-Nitro-4-(4'-phenylaminosulphonylphenyl)-phenyl | —CH₃ | —CN | —CH₂CH₂OH |
| 388 | 4-(2',4'-Dinitrophenylamino)-phenyl | " | " | " |
| 389 | 4-(4'-Acetylaminophenyl)-phenyl | " | " | —CH₂CH₂CN |
| 390 | 6-Dimethylaminosulphonyl-naphthyl-2 | " | " | —CH₃ |
| 391 | 2-Ethoxynaphthy-1 | " | " | " |
| 392 | 4-Phenylazophenyl | Pyridyl-3 | " | —C₂H₅ |
| 393 | 5-Nitrothiazolyl-2 | Thienyl-2 | " | —CH₃ |
| 394 | " | " | " | —N(CH₃)₂ |
| 395 | " | " | " | —C₂H₅ |
| 396 | 3-Methylthiadiazolyl-5 | Thiazolyl-5 | —COC₂H₅ | —C₃H₇ |
| 397 | Benzothiazolyl-2 | Thienyl-2 | —CN | —C₂H₅ |
| 398 | 3-Methylthiadiazolyl-5 | Thiazolyl-5 | —SO₂CH₃ | —NHCH₂CH₂OH |
| 399 | " | " | —CN | —NHCH₂CH₂OC₂H₅ |
| 400 | 2-Acetyl-4-nitrothienyl-5 | Pyridyl-3 | " | N-Piperidyl |
| 401 | " | " | " | —CH₃ |
| 402 | 4-Methyl-5-cyanothiazolyl-2 | " | " | —C₂H₅ |
| 403 | 6-Ethoxybenzothiazolyl-2 | —CH₃ | —SO₂CH₃ | N-Piperidyl |
| 404 | " | Thienyl-2 | —CN | —C₂H₅ |
| 405 | 6-Nitrobenzothiazolyl-2 | " | " | —N(C₂H₅)₂ |
| 406 | " | Pyridyl-3 | " | N-Morpholinyl |
| 407 | 5-Nitrothiazolyl-2 | Benzoimidazolyl-2 | " | —N(CH₂CH₂CN)₂ |
| 408 | 1-Methyl-4-cyanopyrazolyl-5 | Furyl | " | " |
| 409 | 6-Methylsulphonylbenzothiazolyl-2 | Thienyl-2 | —SO₂C₆H₅ | —CH₂CH(CH₃)₂ |
| 410 | 6-Cyanoethylsulfonylbenzothiazolyl-2 | " | —CN | —CH₂CH₂OCOCH₃ |
| 411 | " | " | " | —CH₂CH₂COOCH₃ |
| 412 | 1-Methylimidazolyl-2 | Thiazolyl-5 | —COC₆H₅ | —C₂H₅ |
| 413 | Thiazolyl-2 | 3-Methylthienyl-2 | —COOC₂H₅ | —N(CH₂CH₂OCOCH₃)₂ |
| 414 | " | " | —CON(C₂H₅)₂ | —CH₃ |

EXAMPLE 415

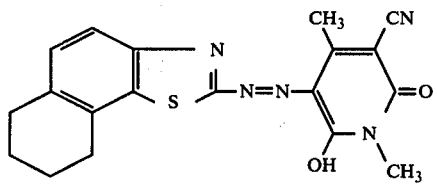

Formulae of representative dyes of the foregoing Examples are as follows:

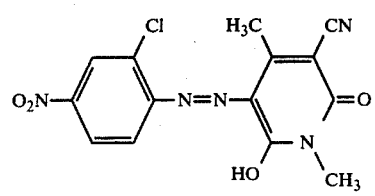

Example 3

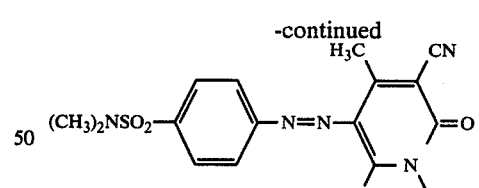

Example 3

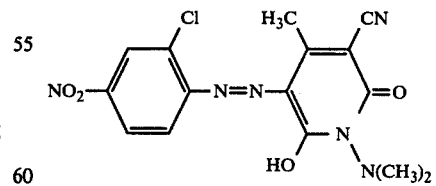

Example 4

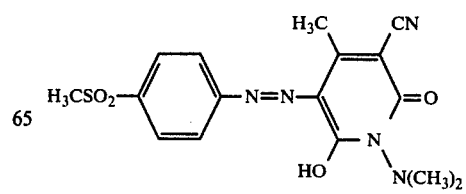

Example 4

Example 361q

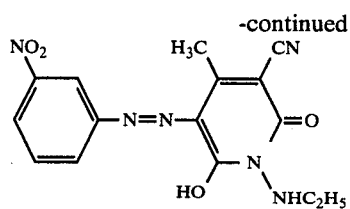

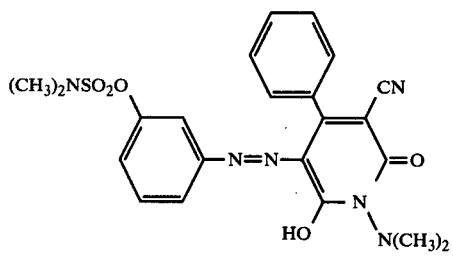

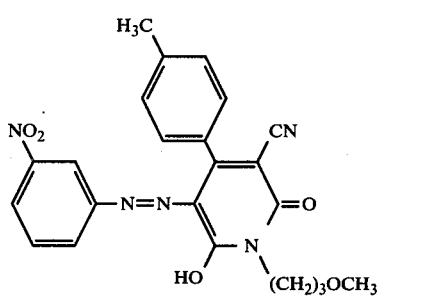

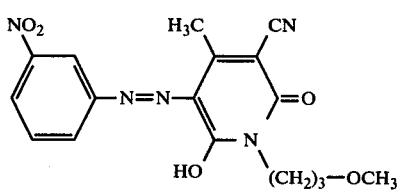

Example 7

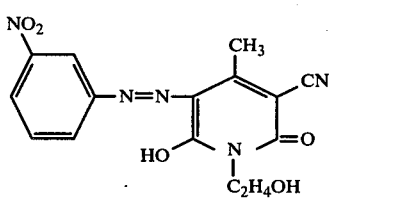

Example 78

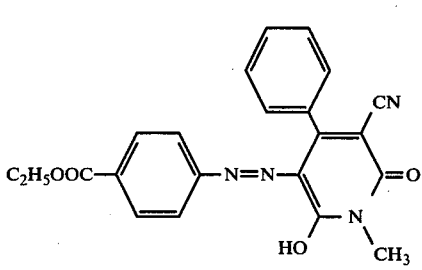

Example 314

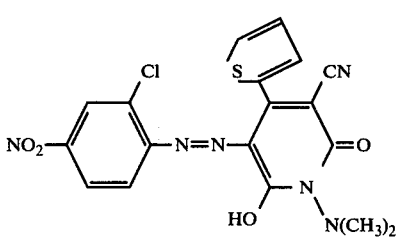

Example 315

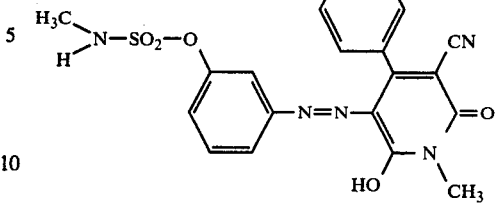

Example 6

Example 7

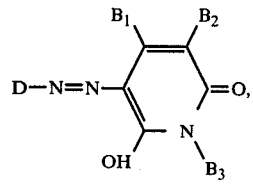

Example 316

Having thus disclosed, the invention what we claim is:

1. A compound of the formula $$\underset{OH}{\overset{B_1 \quad B_2}{D-N=N}} \overset{}{\underset{B_3}{N}} =O,$$

wherein
D is (a) thiazolyl, (b) substituted thiazolyl each substituent of which is independently chloro, bromo, nitro, cyano, methyl, phenyl, methylsulfonyl or ethylsulfonyl, (c) benzothiazolyl, (d) substituted benzothiazolyl each substituent of which is independently chloro, bromo, cyano, nitro, methyl, ethyl, methoxy, ethoxy, methylsulfonyl, ethylsulfonyl, cyanoethylsulfonyl, sulfamoyl or methylsulfamoyl, (e) pyrazolyl, (f) substituted pyrazolyl each substituent of which is independently cyano, methyl or phenyl, (g) thiadiazolyl, (h) methylthiadiazolyl, (i) imidazolyl, (j) substituted imidazolyl each substituent of which is independently nitro or methyl, (k) thienyl, (l) substituted thienyl each substituent of which is independently nitro or acetyl or (m) 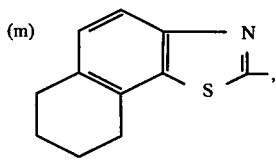

$B_1$ is (a) alkyl of 1 to 4 carbon atoms, (b) substituted alkyl of 1 to 4 carbon atoms each substituent of which is independently chloro, bromo, hydroxy, cyano, methoxy or ethoxy, (c) phenyl, (d) substituted phenyl each substituent of which is independently chloro, bromo, methyl, methoxy, nitro, methoxycarbonyl, ethoxycarbonyl, methylsulfamoyl, dimethylsulfamoyl, cyano or acetamido, (e) naphthyl, (f) methoxynaphthyl, (g) ethoxynaphthyl, (h) thienyl, (i) methylthienyl, (j) furyl, (k) thiazolyl, (l) pyridyl, (m) imidazolyl or (n) benzimidazolyl, $B_2$ is cyano, acetyl, propionyl, methylsulfonyl, ethylsulfonyl, benzoyl, phenylsulfonyl, nicotinoyl, carbamoyl, methylcarbamoyl, dimethylcarbamoyl, ethylcarbamoyl or diethylcarbamoyl, and $B_3$ is (a) alkyl of 1 to 4 carbon atoms, (b) substituted alkyl of 1 to 4 carbon atoms each substituent of which is independently chloro, bromo, hydroxy, cyano, methoxy, ethoxy, methoxyethoxy, cyanoethoxy, phenoxyethoxy, acetyl, propionyl, benzoyl, formyloxy, acetoxy, propionyloxy, methoxypropionyloxy, acryloyloxy, benzoyloxy, methoxycarbonyl, ethoxycarbonyl, ethoxyethoxycarbonyl, cyanomethoxycarbonyl, phenoxycarbonyl, methoxycarbonyloxy, ethoxycarbonyloxy, phenoxycarbonyloxy, carbamoyl, methylcarbamoyl, dimethylcarbamoyl, methylcarbamoyloxy, ethylcarbamoyloxy, phenylcarbamoyloxy, methoxycarbonylethoxy, 5-chlorofuryl-2-, methylsulfonyloxy, ethylsulfonyloxy, phenylsulfonyloxy, vinylsulfonyloxy, phenoxysulfonyl, phenthioethylsulfonyl or vinylsulfonyl, (c) cyclohexyl, (d) trimethylcyclohexyl, (e) methylamino, (f) dimethylamino, (g) ethylamino, (h) diethylamino, (i) hydroxyethylamino, (j) di-(β-cyanoethyl)amino, (k) di(acetoxyethyl)amino, (l) phenylamino, (m) ethoxyethylamino, (n) formamido, (o) acetamido, (p) propionamido, (q) benzamido, (r) N-piperazino, (s) N-piperidino, (t) N-morpholino or

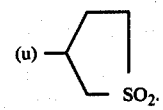

(u)

2. A compound of the formula

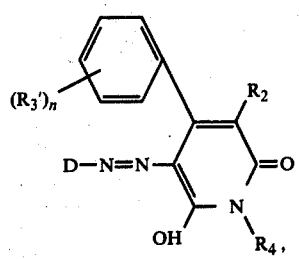

wherein
D is substituted phenyl, wherein each substituent of substituted phenyl is chloro, bromo, nitro, lower alkyl, lower alkoxy, cyano, lower alkoxycarbonyl, sulfamoyl, N-lower alkylsulfamoyl, N,N-dilower alkylsulfamoyl, N-lower alkylsulfamoyloxy or N,N-dilower alkylsulfamoyloxy,
$R_2$ is cyano or lowr alkanoyl,
$R_3'$ is chloro, lower alkyl or lower alkoxy,
$R_4$ is lower alkyl or lower alkyl monosubstituted by hydroxy or lower alkoxy, and
n is 0 or 1.

3. A compound of the formula

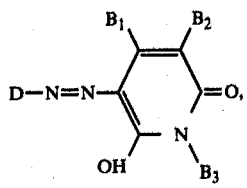

wherein
D is (a) phenyl, (b) substituted phenyl each substituent of which is independently chloro, bromo, hydroxy, cyano, thiocyano, nitro, methyl, ethyl, trifluoromethyl, methoxy, ethoxy, formyl, acetyl, propionyl, benzoyl, methylbenzoyl, methoxycarbonyl, ethoxycarbonyl, ethoxycarbonyloxy, benzyloxycarbonyloxy, acetoxy, propionyloxy, benzoyloxy, methoxyethoxycarbonyl, acetamido, propionamido, benzamido, methoxycarbonylamino, ethoxycarbonylamino, methylsulfonyl, ethylsulfonyl, propylsulfonyl, butylsulfonyl, chloromethylsulfonyl, sulfamoyl, methylsulfamoyl, dimethylsulfamoyl, di-(hydroxyethyl)sulfamoyl, cyclohexylsulfamoyl, phenylsulfamoyl, chloromethylsulfamoyl, methoxyphenylsulfamoyl, benzylsulfamoyl, N-piperidinosulfonyl, N-morpholinosulfonyl, methylsulfonyloxy, ethylsulfonyloxy, ethoxyethylsulfonyloxy, propylsulfonyloxy, hexylsulfonyloxy, cyclohexylsulfonyloxy, cyanoethylsulfonyloxy, phenylsulfonyloxy, chloromethylsulfonyloxy, sulfamoyloxy, N-morpholinosulfonyloxy, methoxyphenylsulfonyloxy, ethyleneaminosulfonyloxy, methylsulfamoyloxy, ethylsulfamoyloxy, propylsulfamoyloxy, butylsulfamoyloxy, dimethylsulfamoyloxy, diethylsulfamoyloxy, dipropylsulfamoyloxy, dibutylsulfamoyloxy, phenylsulfamoyloxy, N-phenyl-N-methylsulfamoyloxy, N-phenyl-N-ethylsulfamoyloxy, methoxyphenylsulfamoyloxy, phenylamino, nitrophenylamino, dinitrophenylamino, phenyl, acetamidophenyl, phenylsulfamoylphenyl, phenylazo or nitrophenylazo, (c) naphthyl, (d) substituted naphthyl each substituent of which is independently methoxy, ethoxy, phenylazo or dimethylsulfamoyl, (e) thiazolyl, (f) substituted thiazolyl each substituent of which is independently chloro, bromo, nitro, cyano, methyl, phenyl, methylsulfonyl or ethylsulfonyl, (g) benzothiazolyl, (h) substituted benzothiazolyl each substituent of which is independently chloro, bromo, cyano, nitro, methyl, ethyl, methoxy, ethoxy, methylsulfonyl, ethylsulfonyl, cyanoethylsulfonyl, sulfamoyl or methylsulfamoyl, (i) pyrazolyl, (j) substituted pyrazolyl each substituent of which is independently cyano, methyl or phenyl, (k) thiadiazolyl, (l) methylthiadiazolyl, (m) imidazolyl, (n) substituted imidazolyl each substituent of which is independently nitro or methyl, (o) thienyl, (p) substituted thienyl each substituent of which is independently nitro or acetyl or

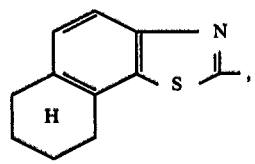

(q)

$B_1$ is (a) alkyl of 1 to 4 carbon atoms, (b) substituted alkyl of 1 to 4 carbon atoms each substituent of which is independently chloro, bromo, hydroxy, cyano, methoxy or ethoxy, (c) phenyl, (d) substituted phenyl each substituent of which is independently chloro, bromo, methyl, methoxy, nitro, methoxycarbonyl, ethoxycarbonyl, methylsulfamoyl, dimethylsulfamoyl, cyano or acetamido, (e) naphthyl, (f) methoxynaphthyl, (g) ethoxynaphthyl, (h) thienyl, (i) methylthienyl, (j) furyl, (k) thiazolyl, (l) pyridyl, (m) imidazolyl or (n) benzimidazolyl,
$B_2$ is cyano, acetyl, propionyl, methylsulfonyl, ethylsulfonyl, benzoyl, phenylsulfonyl, nicotinoyl, carbamoyl, methylcarbamoyl, dimethylcarbamoyl, ethylcarbamoyl or diethylcarbamoyl, and B₃ is methylamino, dimethylamino, ethylamino, diethylamino, hydroxyethylamino, di-(β-cyanoethyl)amino, di-(acetoxyethyl)amino, phenylamino, ethoxyethylamino, formamido, acetamido, propionamido, benzamido, N-piperazino, N-piperidino or N-morpholino.

4. A compound of the formula

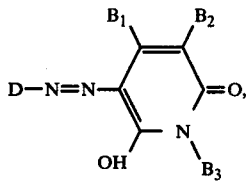

wherein

D is (a) phenyl, (b) substituted phenyl each substituent of which is independently chloro, bromo, hydroxy, cyano, thiocyano, nitro, methyl, ethyl, trifluoromethyl, methoxy, ethoxy, formyl, acetyl, propionyl, benzoyl, methylbenzoyl, methoxycarbonyl, ethoxycarbonyl, ethoxycarbonyloxy, benzyloxycarbonyloxy, acetoxy, propionyloxy, benzoyloxy, methoxyethoxycarbonyl, acetamido, propionamido, benzamido, methoxycarbonylamino, ethoxycarbonylamino, methylsulfonyl, ethylsulfonyl, propylsulfonyl, butylsulfonyl, chloromethylsulfonyl, sulfamoyl, methylsulfamoyl, dimethylsulfamoyl, di-(hydroxyethyl)sulfamoyl, cyclohexylsulfamoyl, phenylsulfamoyl, chloromethylsulfamoyl, methoxyphenylsulfamoyl, benzylsulfamoyl, N-piperidinosulfonyl, N-morpholinosulfonyl, methylsulfonyloxy, ethylsulfonyloxy, ethoxyethylsulfonyloxy, propylsulfonyloxy, hexylsulfonyloxy, cyclohexylsulfonyloxy, cyanoethylsulfonyloxy, phenylsulfonyloxy, chloromethylsulfonyloxy, sulfamoyloxy, N-morpholinosulfonyloxy, methoxyphenylsulfonyloxy, ethyleneaminosulfonyloxy, methylsulfamoyloxy, ethylsulfamoyloxy, propylsulfamoyloxy, butylsulfamoyloxy, dimethylsulfamoyloxy, diethylsulfamoyloxy, dipropylsulfamoyloxy, dibutylsulfamoyloxy, phenylsulfamoyloxy, N-phenyl-N-methylsulfamoyloxy, N-phenyl-N-ethylsulfamoyloxy, methoxyphenylsulfamoyloxy, phenylamino, nitrophenylamino, dinitrophenylamino, phenyl, acetamidophenyl, phenylsulfamoylphenyl, phenylazo or nitrophenylazo, (c) naphthyl, (d) substituted naphthyl each substituent of which is independently methoxy, ethoxy, phenylazo or dimethylsulfamoyl, (e) thiazolyl, (f) substituted thiazolyl each substituent of which is independently chloro, bromo, nitro, cyano, methyl, phenyl, methylsulfonyl or ethylsulfonyl, (g) benzothiazolyl, (h) substituted benzothiazolyl each substituent of which is independently chloro, bromo, cyano, nitro, methyl, ethyl, methoxy, ethoxy, methylsulfonyl, ethylsulfonyl, cyanoethylsulfonyl, sulfamoyl or methylsulfamoyl, (i) pyrazolyl, (j) substituted pyrazolyl each substituent of which is independently cyano, methyl or phenyl, (k) thiadiazolyl, (l) methylthiadiazolyl, (m) imidazolyl, (n) substituted imidazolyl each substituent of which is independently nitro or methyl, (o) thienyl, (p) substituted thienyl each substituent of which is independently nitro or acetyl or

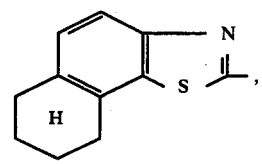

B₁ is (a) alkyl of 1 to 4 carbon atoms, (b) substituted alkyl of 1 to 4 carbon atoms each substituent of which is independently chloro, bromo, hydroxy, cyano, methoxy or ethoxy, (c) phenyl, (d) substituted phenyl each substituent of which is independently chloro, bromo, methyl, methoxy, nitro, methoxycarbonyl, ethoxycarbonyl, methylsulfamoyl, dimethylsulfamoyl, cyano or acetamido, (e) naphthyl, (f) methoxynaphthyl, (g) ethoxynaphthyl, (h) thienyl, (i) methylthienyl, (j) furyl, (k) thiazolyl, (l) pyridyl, (m) imidazolyl or (n) benzimidazolyl, B₂ is methylsulfonyl, ethylsulfonyl or phenylsulfonyl, and B₃ is (a) alkyl of 1 to 4 carbon atoms, (b) substituted alkyl of 1 to 4 carbon atoms each substituent of which is independently chloro, bromo, hydroxy, cyano, methoxy, ethoxy, methoxyethoxy, cyanoethoxy, phenoxyethoxy, acetyl, propionyl, benzoyl, formyloxy, acetoxy, propionyloxy, methoxypropionyloxy, acryloxy, benzoyloxy, methoxycarbonyl, ethoxycarbonyl, ethoxyethoxycarbonyl, cyanomethoxycarbonyl, phenoxycarbonyl, methoxycarbonyloxy, ethoxycarbonyloxy, phenoxycarbonyloxy, carbamoyl, methylcarbamoyl, dimethylcarbamoyl, methylcarbamoyloxy, ethylcarbamoyloxy, phenylcarbamoyloxy, methoxycarbonylethoxy, 5-chlorofuryl-2-, methylsulfonyloxy, ethylsulfonyloxy, phenylsulfonyloxy, vinylsulfonyloxy, phenoxysulfonyl, phenthioethylsulfonyl or vinylsulfonyl, (c) cyclohexyl, (d) trimethylcyclohexyl, (e) methylamino, (f) dimethylamino, (g) ethylamino, (h) diethylamino, (i) hydroxyethylamino, (j) di-(β-cyanoethyl)amino, (k) di(acetoxyethyl)amino, (l) phenylamino, (m) ethoxyethylamino, (n) formamido, (o) acetamido (p) propionamido, (q) banzamido, (r) N-piperazino, (s) N-piperidino, (t) N-morpholino or

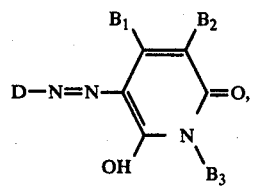

5. A compound of the formula

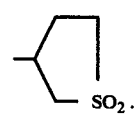

wherein

D is (a) phenyl, (b) substituted phenyl each substituent of which is independently chloro, bromo, hydroxy, cyano, thiocyano, nitro, methyl, ethyl, trifluoromethyl, methoxy, ethoxy, formyl, acetyl, propionyl, benzoyl, methylbenzoyl, methoxycarbonyl, ethoxycarbonyl, ethoxycarbonyloxy, benzyloxycarbonyloxy, acetoxy, propionyloxy, benzoyloxy, methoxyethoxycarbonyl, acetamido, propionamido, benzamido, methoxycarbonylamino, ethoxycarbonylamino, methylsulfonyl, ethylsulfonyl, propylsulfonyl, butylsulfonyl, chloromethylsulfonyl, sulfamoyl, methylsulfamoyl, dimethylsulfamoyl, di-(hydroxyethyl)sulfamoyl, cyclohexylsulfamoyl, phenylsulfamoyl, chloromethylsulfamoyl, methoxyphenylsulfamoyl, benzylsulfamoyl, N-piperidinosulfonyl, N-morpholinosulfonyl, methylsulfonyloxy, ethylsulfonyloxy, ethoxyethylsulfonyloxy, propylsulfonyloxy, hexylsulfonyloxy, cyclohexylsulfonyloxy, cyanoethylsulfonyloxy, phenylsulfonyloxy, chloromethylsulfonyloxy, sulfamoyloxy, N-morpholinosulfonyloxy, methoxyphenylsulfonyloxy, ethyleneaminosulfonyloxy, methylsulfamoyloxy, ethylsulfamoyloxy, propylsulfamoyloxy, butylsulfamoyloxy, dimethylsulfamoyloxy, diethylsulfamoyloxy, dipropylsulfamoyloxy, dibutylsulfamoyloxy, phenylsulfamoyloxy, N-phenyl-N-methylsulfamoyloxy, N-phenyl-N-ethylsulfamoyloxy, methoxyphenylsulfamoyloxy, phenylamino, nitrophenylamino, dinitrophenylamino, phenyl, acetamidophenyl or phenylsulfamoylphenyl, (c) naphthyl, (d) substituted naphthyl each substituent of which is independently methoxy, ethoxy, phenylazo or dimethylsulfamoyl, (e) thiazolyl, (f) substituted thiazolyl each substituent of which is independently chloro, bromo, nitro, cyano, methyl, phenyl, methylsulfonyl or ethylsulfonyl, (g) benzothiazolyl, (h) substituted benzothiazolyl each substituent of which is independently chloro, bromo, cyano, nitro, methyl, ethyl, methoxy, ethoxy, methylsulfonyl, ethylsulfonyl, cyanoethylsulfonyl, sulfamoyl or methylsulfamoyl, (i) pyrazolyl, (j) substituted pyrazolyl each substituent of which is independently cyano, methyl or phenyl, (k) thiadiazolyl, (l) methylthiadiazolyl, (m) imidazolyl, (n) substituted imidazolyl each substituent of which is independently nitro or methyl, (o) thienyl, (p) substituted thienyl each substituent of which is independently nitro or acetyl or

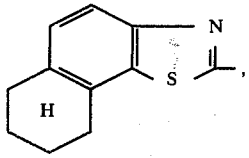   (q)

B₁ is (a) phenyl, (b) substituted phenyl each substituent of which is independently chloro, bromo, methyl, methoxy, nitro, methoxycarbonyl, ethoxycarbonyl, methylsulfamoyl, dimethylsulfamoyl, cyano or acetamido, (c) naphthyl, (d) methoxynaphthyl, (e) ethoxynaphthyl, (f) thienyl, (g) methylthienyl, (h) furyl, (i) thiazolyl, (j) pyridyl, (k) imidazolyl or (l) benzimidazolyl, B₂ is cyano, acetyl, propionyl, methylsulfonyl, ethylsulfonyl, benzoyl, phenylsulfonyl, nicotinoyl, carbamoyl, methylcarbamoyl, dimethylcarbamoyl, ethylcarbamoyl or diethylcarbamoyl, and B₃ is (a) alkyl of 1 to 4 carbon atoms, (b) substituted alkyl of 1 to 4 carbon atoms each substituent of which is independently chloro, bromo, hydroxy, cyano, methoxy, ethoxy, methoxyethoxy, cyanoethoxy, phenoxyethoxy, acetyl, propionyl, benzoyl, formyloxy, acetoxy, propionyloxy, methoxypropionyloxy, acryloxy, benzoyloxy, methoxycarbonyl, ethoxycarbonyl, ethoxyethoxycarbonyl, cyanomethoxycarbonyl, phenoxycarbonyl, methoxycarbonyloxy, ethoxycarbonyloxy, phenoxycarbonyloxy, carbamoyl, methylcarbamoyl, dimethylcarbamoyl, methylcarbamoyloxy, ethylcarbamoyloxy, phenylcarbamoyloxy, methoxycarbonylethoxy, 5-chlorofuryl-2-, methylsulfonyloxy, ethylsulfonyloxy, phenylsulfonyloxy, vinylsulfonyloxy, phenoxysulfonyl, phenthioethylsulfonyl or vinylsulfonyl, (c) cyclohexyl, (d) trimethylcyclohexyl, (e) methylamino, (f) dimethylamino, (g) ethylamino, (h) diethylamino, (i) hydroxyethylamino, (j) di-(β-cyanoethyl)amino, (k) di(acetoxyethyl)amino, (l) phenylamino, (m) ethoxyethylamino, (n) formamido, (o) acetamido, (p) propionamido, (q) benzamido, (r) N-piperazino, (s) N-piperidino, (t) N-morpholino or

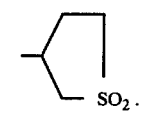   (u)

6. The compound according to claim 3 having the formula

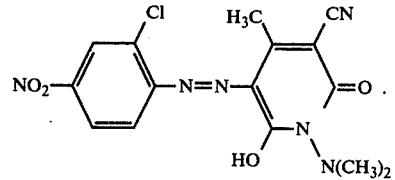

7. The compound according to claim 3 having the formula

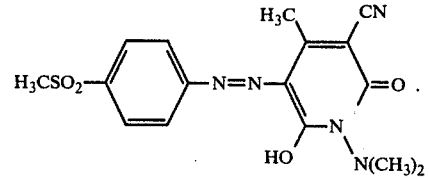

8. The compound according to claim 3 having the formula

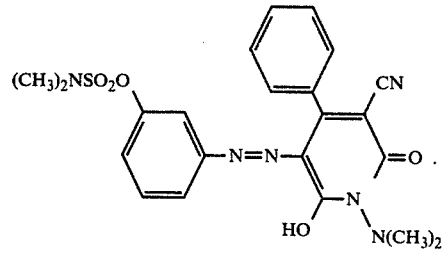

9. The compound according to claim 3 having the formula
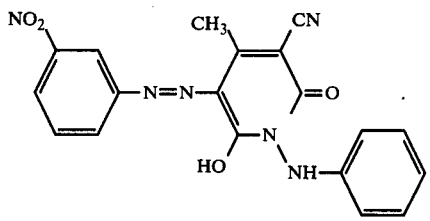
10. The compound according to claim 5 having the formula
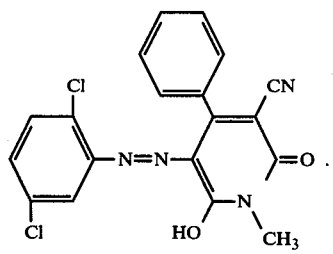
11. The compound according to claim 5 having the formula
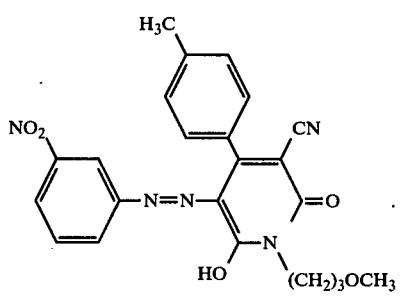
12. The compound according to claim 5 having the formula
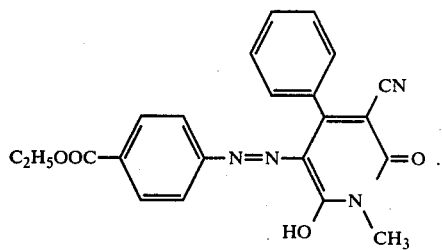
13. The compound of the formula
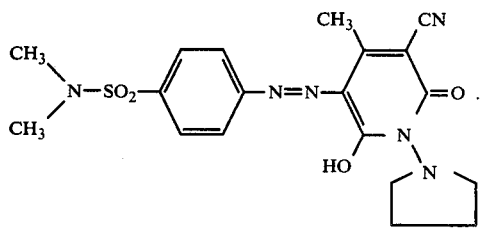
14. The compound the formula
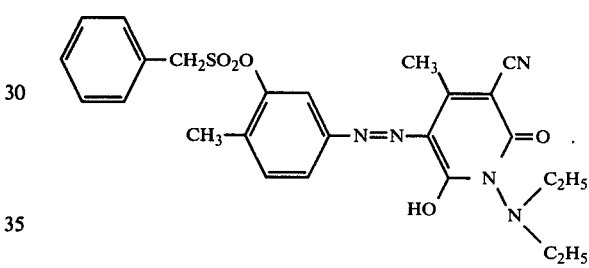
15. The compound according to claim 3 having the formula
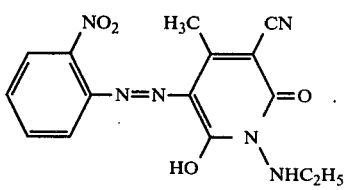
16. The compound of the formula
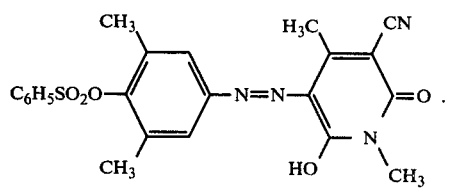
* * * * *